United States Patent
Bair et al.

[11] Patent Number: 6,126,668
[45] Date of Patent: Oct. 3, 2000

[54] MICROKERATOME

[75] Inventors: Scott S. Bair, Atlanta, Ga.; Igor Gradov, Alamo, Calif.; Ronald L. Rabie, Los Alamos, N. Mex.; Edward Larry Hicks, Lilburn, Ga.

[73] Assignee: Innovative Optics, Inc., Albuquerque, N. Mex.

[21] Appl. No.: 09/066,496

[22] Filed: Apr. 24, 1998

Related U.S. Application Data

[60] Provisional application No. 60/044,897, Apr. 25, 1997, and provisional application No. 60/062,116, Oct. 14, 1997.

[51] Int. Cl.$^7$ ..................................................... A61B 17/32
[52] U.S. Cl. ........................................... 606/166; 606/169
[58] Field of Search .................... 606/107, 166, 606/167, 169, 4, 5, 6, 171

[56] References Cited

U.S. PATENT DOCUMENTS

| | | |
|---|---|---|
| 1,987,907 | 1/1935 | Jenkins . |
| 3,542,017 | 11/1970 | Adams . |
| 3,547,110 | 12/1970 | Balamuth . |
| 3,566,869 | 3/1971 | Crowson . |
| 3,589,363 | 6/1971 | Banko . |
| 3,614,953 | 10/1971 | Moss . |
| 3,693,613 | 9/1972 | Kelman . |
| 3,818,913 | 6/1974 | Wallach . |
| 3,944,341 | 3/1976 | Pomerantzeff . |
| 4,137,920 | 2/1979 | Bonnet . |
| 4,138,191 | 2/1979 | Peyman et al. . |
| 4,157,859 | 6/1979 | Terry . |
| 4,406,285 | 9/1983 | Villasenor et al. . |
| 4,445,892 | 5/1984 | Hussein et al. . |
| 4,461,294 | 7/1984 | Baron . |
| 4,469,098 | 9/1984 | Davi . |
| 4,526,171 | 7/1985 | Schachar .................................. 128/305 |
| 4,546,773 | 10/1985 | Kremer et al. . |
| 4,648,400 | 3/1987 | Schneider et al. . |
| 4,662,370 | 5/1987 | Hoffmann et al. ...................... 128/305 |
| 4,665,913 | 5/1987 | L'Esperance, Jr. . |
| 4,669,466 | 6/1987 | L'Esperance . |
| 4,688,570 | 8/1987 | Kramer et al. . |
| 4,705,037 | 11/1987 | Peyman et al. . |
| 4,718,418 | 1/1988 | L'Esperance, Jr. . |
| 4,729,372 | 3/1988 | L'Esperance, Jr. . |
| 4,732,148 | 3/1988 | L'Esperance, Jr. . |
| 4,815,463 | 3/1989 | Hanna . |
| 4,884,570 | 12/1989 | Krumeich et al. . |
| 5,108,412 | 4/1992 | Krumeich et al. . |
| 5,133,726 | 7/1992 | Ruiz et al. . |
| 5,288,292 | 2/1994 | Giraud et al. . |
| 5,368,604 | 11/1994 | Kilmer et al. . |
| 5,441,511 | 8/1995 | Hanna . |
| 5,441,512 | 8/1995 | Muller ...................................... 606/169 |
| 5,496,339 | 3/1996 | Koepnick . |
| 5,586,980 | 12/1996 | Kremer et al. ............................. 606/4 |
| 5,591,174 | 1/1997 | Clark et al. . |
| 5,611,805 | 3/1997 | Hall . |
| 5,658,303 | 8/1997 | Koepnick . |
| 5,779,723 | 7/1998 | Schwind .................................. 606/166 |
| 5,980,543 | 11/1999 | Carriazo et al. ........................ 606/166 |
| 5,997,559 | 12/1999 | Ziemer .................................... 606/166 |

FOREIGN PATENT DOCUMENTS

WO 93/06789  4/1993  European Pat. Off. .

OTHER PUBLICATIONS

Derwent Publications, Ltd., Hanna K, FR2595243, (Sep. 11, 1987), Abstract.

*Primary Examiner*—Wynn Wood Coggins
*Assistant Examiner*—Jennifer Maynard
*Attorney, Agent, or Firm*—Jones & Askew

[57] ABSTRACT

A microkeratome is provided for use in lamellar surgery on the cornea of the eye. The microkeratome includes a base carrying a camshaft for rotation by a cable connected to the shaft. The base also supports a moving blade assembly slidably mounted on an applanator assembly, with the blade being thin and under tension. The moving blade assembly moves above and sidewardly relative to a suction ring. The moving blade assembly is sized to oscillate side-to-side approximately 1 mm. The moving blade assembly is driven by a connecting cable, wherein longitudinal movement of the cable produces responsive longitudinal movement of the frame and blade to cut a flap or disc of a desired configuration.

4 Claims, 21 Drawing Sheets

(BLADE WITHDRAWN)

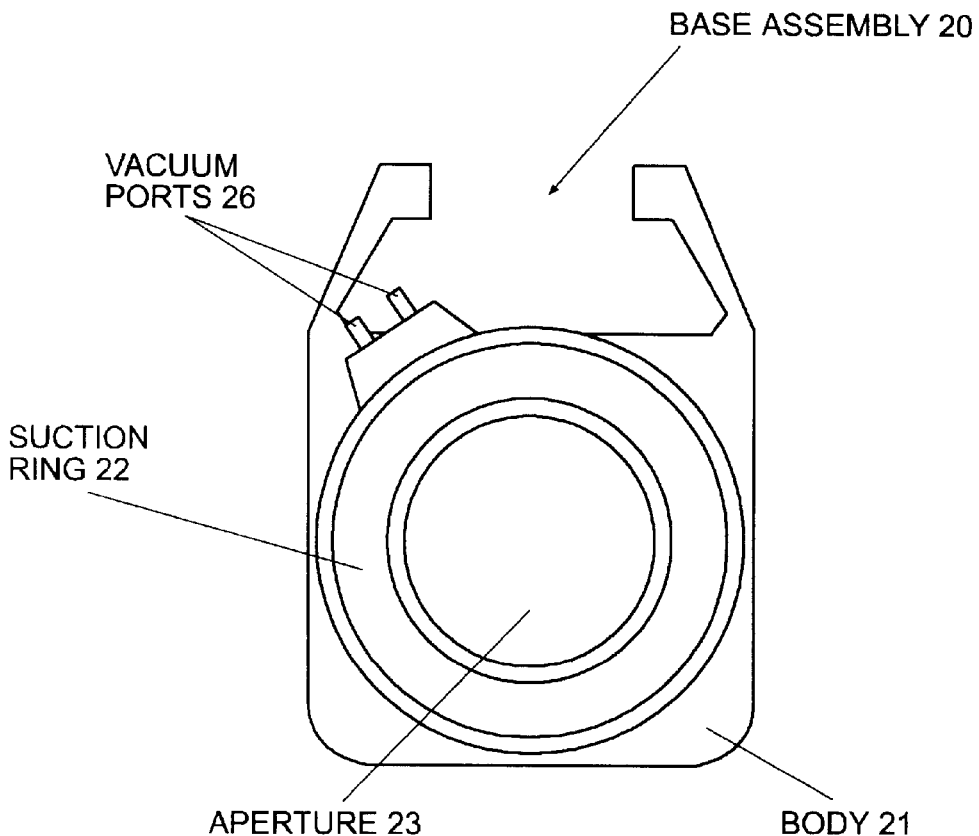
Fig. 6
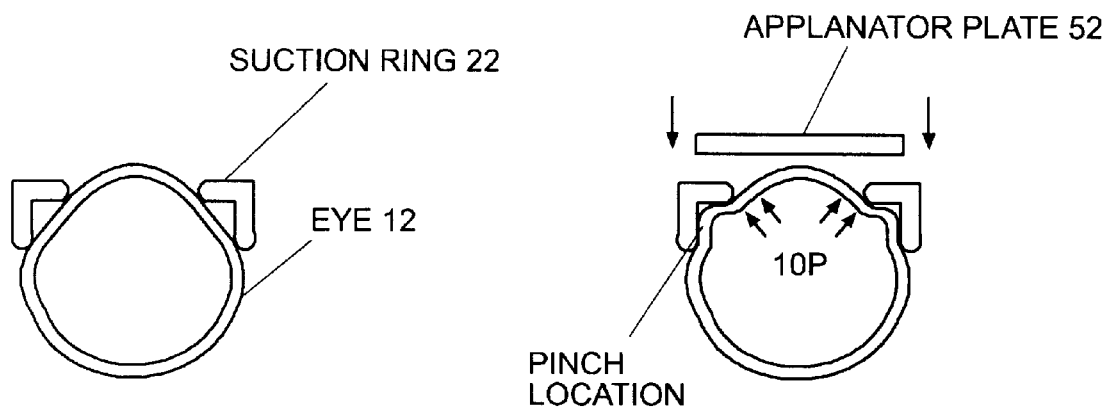
Fig. 7A  Fig. 7B

HINGED APPLANATOR ALLOWS FOR
REPLACEMENT OF BLADE ASSY AND SHOE
ALSO ALLOWS TO PRESSURE MEASURMENT
WITH SEPARATE INSTRUMENT

ADJUSTABLE APPLANATOR CHANGES APPLICATION DISC DIAMETER

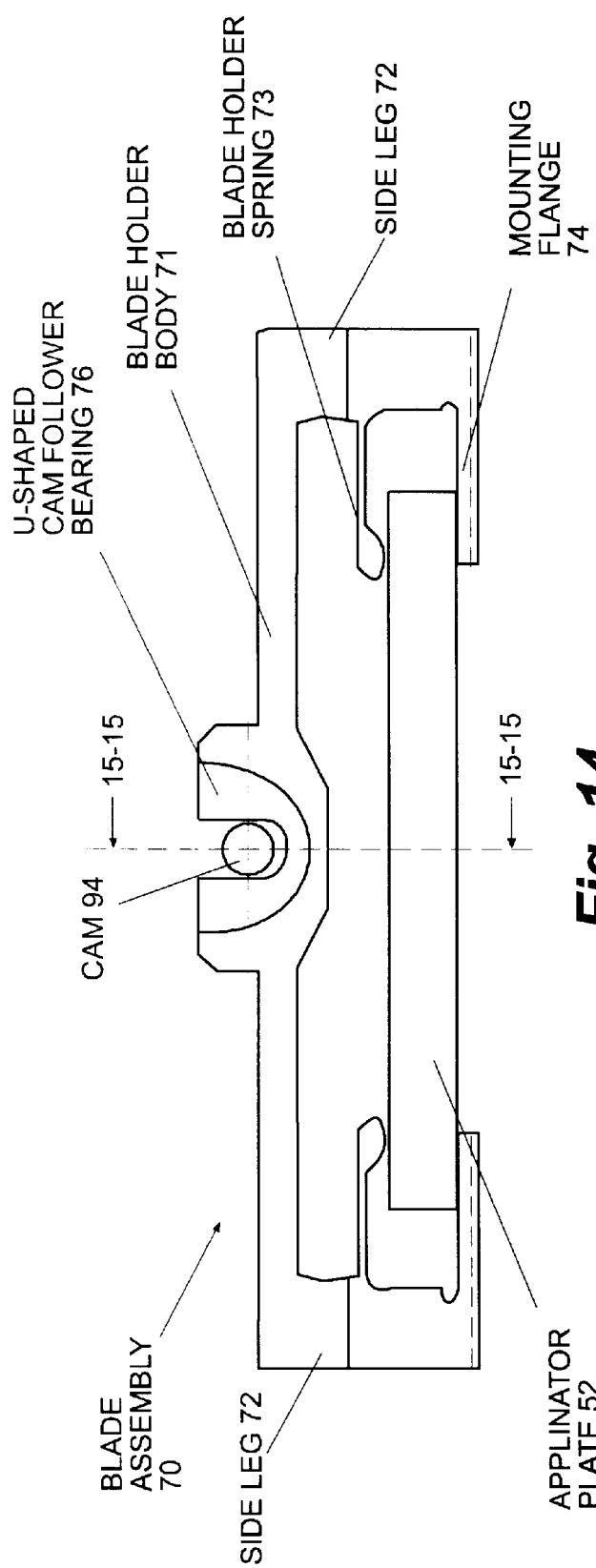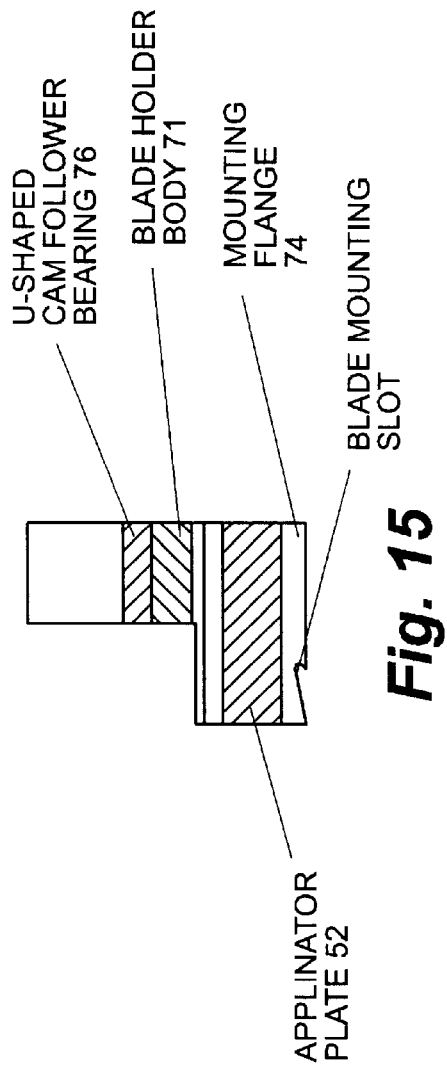

Mold from plastic

Cannot be installed backwards

For I.O.P. measurement at applanator working surface.

SECTION VIEW
ALONG COUNTERBORE C/L

TOP VIEW improved bearings

MODULAR CABLE DRIVE ASSEMBLY

ROTATING SHEATH CLAMP FREE TO ROTATE-
REMOVES ROTATIONAL TORQUE TO SURGEON

MICROKERATOME

CROSS REFERENCE TO RELATED APPLICATIONS

This application claims the benefit of earlier-filed provisional application Ser. No. 60/044,897, filed Apr. 25, 1997 and Ser. No. 60/062,116, filed Oct. 14, 1997.

FIELD OF THE INVENTION

This invention generally relates to corneal surgery, and particularly relates to a microkeratome for use in lamellar corneal surgery.

BACKGROUND OF THE INVENTION

This eye includes, inter alia, a cornea and a lens, separated by an anterior space. Each of these components provides optical refraction for proper vision. Defects in vision may result from a misshaped cornea which fails to provide the necessary refraction. For example, myopia (nearsightedness) occurs when the visual images come into focus in front of the retina of the eye, and this results in distant objects being viewed as out of focus. Hyperopia (farsightedness) occurs when the focal point of visual images is behind the retina of the eye, resulting in difficulty in viewing nearby objects. Astigmastism is an optical defect which occurs when an optical component such as the cornea or lens is irregularly shaped and the rays of the visual image fail to meet in a focal point, resulting in a blurred and imperfect image.

These defects have been treated in a variety of ways. Eyeglasses or contact lenses have been used, but may be expensive or inconvenient, or require changes as the visual acuity of the eye changes over time, and are practical only for humans and not in veterinary applications.

In more recent developments, myopia and astigmatism have been treated by a surgical procedure known as radial keratotomy. This procedure involves making radical cuts in the cornea from a central optical zone to change its shape. Many patients have reported satisfactory results, but the procedure not only requires great skill by the opthamologist but also weakens the cornea. It is also limited to about 8 diopters of refractive correction, and the patient may experience some reflection from the incisions resulting in degradation of night vision.

Another surgical solution which has been advanced uses eximer lasers to sculpt the cornea. By removing selected portions of the cornea through vaporization, the surgeon may correct the patient's vision. This involves scraping the epithelium (the thin outer layer over the cornea) away and then the eximer laser ablates the cornea. Unfortunately, this procedure is painful to the patient because of damage to the epithelium and Bowman's membrane, and requires a great deal of surgical skill, as well as involving delicate and expensive equipment.

As a result of certain drawbacks in other procedures, a technique enjoying increased popularity is lamellar surgery, which involves making lamellar (disk) cuts in the eye, and then removing and reshaping the disc before reattachment. The cut disk was frozen, reshaped and replaced in a procedure first developed by Dr. Barraquer known as keratomileusis. Later developments have refined this procedure and have attempted to overcome deficiencies in the technique. One recognized improvement has been the removal and retention of the uppermost layer of the cornea. This uppermost layer includes the epithelium and the Bowman's layer or membrane, which should be replaced for optimal healing of the eye. Removal of the epithelium and Bowman's membrane exposes the stroma of the cornea. The microkeratome removes a disc from the stroma of the desired thickness, and the surgeon then replaces the epithelium and Bowman's membrane like a cap over the lamellar cut. The preservation of the Bowman's membrane and epithelium allows the epithelial cells to reattach the cap over the stromal bed. More recent techniques, known as laser assisted in-situ keratomileusis (LASIK) uses a combination of the lamellar technique and eximer laser technique whereby after removal of the cap, the eximer laser ablates the stromal bed to provide the desired refractive correction, then the cap is replaced as described above.

A number of different keratomes have heretofore been developed, as shown, for example, in U.S. Pat. No. 5,591,174 to Clark et al.; U.S. Pat. No. 5,496,339 to Koepnick; U.S. Pat. No. 5,288,292 to Giraud, et al.; U.S. Pat. No. 5,133,726 to Ruiz et al.; U.S. Pat. No. 4,884,570 to Krumeich et al; and U.S. Pat. No. 4,662,370 to Hoffman et al.; and also in published International Application No. WO 93/06783. These keratomes involve a blade which oscillates from side to side to cut through the cornea as the blade moves longitudinally. The blade is typically driven by a cam and slot arrangement, the cam being connected to a motor drive. The blade is located beneath an applanator surface which flattens the arcuate surface of the eye for performing the cut, and also increases the interocular pressure within the eye, which is critical to a successful cut of the cornea. The depth of the disc cut is very precise, measured in microns, to provide proper optical correction.

Several problems are presented by such prior art microkeratomes. One problem is the weight of the instrument which is placed on the eye. The eye is coated with a lubricating liquid (tears) and the greater the weight borne by the eye, the greater the likelihood the microkeratome will slip.

Slippage of the microkeratome during surgery may have catastrophic results. Current microkeratomes place 5 or 6 ounces (about 150 grams) of weight offset from the eye.

Another problem associated with the current microkeratomes is that fluid may build up beneath the applanator adversely affecting the precision of the cut. The applanator may slide along the cornea during surgery. The sliding applanator should produce a film by hydrodynamic wedge action and when stationary should produce a squeeze film when pressed against the cornea. The possibility exists for a liquid to be entrapped between the blade and the applanator when the liquid film collapses at its edges by leakage. The presence of any liquid film reduces the thickness of the cut by occupying the space between the blade and the applanator. Such entrapment would reduce the thickness the most at the center of the intended cut, and if thicker than the intended thickness of the disc to be cut, then a central region of the cornea will not be cut, resulting in a "button-hole".

Another problem associated with button-holing is the lack of sufficient interocular pressure (IOP).

Another problem is that in prior art devices it is difficult to see the progress of the cut as it is being made. In certain situations this is a severe disadvantage as there is no way to stop the cutting process before damage is done.

SUMMARY OF THE INVENTION

The present invention overcomes deficiencies in the prior art by providing an improved microkeratome which provides an improved cut by providing an improved suction ring, an adjustable applanator, and while allowing the surgeon to view the cut as it is being made, while measuring the interocular pressure of the eye before, during, and after the cutting process.

Generally described, the present invention relates to the use of a microkeratome device, the device comprising a base assembly including a suction ring, an applanator assembly, a knife assembly configured for movement along its cutting edge axis as well as tranverse to its cutting edge axis, and a drive assembly for driving the knife assembly such that the knife moves along both axes, said drive assembly comprised of a single cored sheathed cable.

The present invention also provides a microkeratome device, the device comprising a base assembly including a suction ring, an applanator assembly including an integral pressure transducer, a knife assembly, and a drive assembly for driving the knife assembly such that an eye can be cut.

The present invention further provides a micorkeratome device, the device comprising a base assembly including suction ring, an applanator assembly, a knife assembly, a shoe configured to move in front of said knife assembly, and drive assembly for driving the knife assembly such that eye can be cut.

The present invention also provides a microkeratome device, the device comprising a base assembly including a suction ring, an applanator assembly, a knife assembly, and a drive assembly for driving the knife assembly such that an eye can be cut, the drive assembly including a seismic drive element having irregular distributions suitable to cause said knife assembly to vibrate sufficiently to cause said side-to-side cutting to occur.

The present invention further provides a microkeratome device, the device comprising a base assembly including a suction ring itself including an annular cavity configured to disperse vacuum at least partially around said suction ring even when an eye is fully engaged therein, an applanator assembly, a knife assembly and a drive assembly for driving the knife assembly such that an eye can be cut.

The present invention further provides a microkeratome device, the device comprising a base assembly including a suction ring, the suction ring including a first vacuum port to provide suction sufficient to cause the suction ring to be attached to an eye, the suction ring also including a second vacuum port independent of said second vacuum port routed to a vacuum gauge to detect vacuum, an applanator assembly, a knife assembly, and a drive assembly for driving the knife assembly, such that an eye can be cut.

The present invention further provides a microkeratome device, the device comprising a base assembly including a suction ring, an applanator assembly hingedly removable relative to the base assembly, such that the applanator assembly may be pivoted and then removed from said base assembly while said base assembly is still in place, a knife assembly, and a drive assembly for driving the knife assembly such that an eye can be cut.

The present invention further provides a microkeratome device, the device comprising a base assembly including a suction ring, an applanator assembly, a knife assembly itself comprising a knife and a knife holder holding the knife in tension, and a drive assembly for driving the knife assembly such that an eye can be cut.

In an alternate embodiment, a microkeratome hereof includes a frame, an oscillator comprising an eccentric mount for rotation with a drive connector, an applanator supporting the frame, a blade mount carried by the frame and extending below the applanator, and a blade carried by the applanator for reciprocating movement caused by the oscillator. The applanator is provided with relieved areas on the bottom, eye-engaging side which may be grooves or perforations to allow the conveyance of fluid away from the blade, thereby reducing differences in the depth of the cut at different locations. The microkeratome is used with a suction ring which mounts over the eye and receives the applanator.

In further detail, the alternate applanator is received on the suction ring and held in place thereon by cleats. The blade is located beneath the applanator and is oriented transverse to the longitudinal axis of the suction ring. The frame includes spaced apart feet which serve as guides and are received in tracks extending along each side of the suction ring outboard of the applanator. The feet receive blade clamps which extend below the applanator and secure the blade in tension underneath the applanator. The feet and blade clamps together are narrower than the tracks in the suction ring to permit oscillating movement side-to-side, typically about 1 mm. The frame presents a bridge connecting the guides, the bridge including a central opening. A countershaft passes through the opening and a counterweight is located on the other side. Each of the countershaft and counterweight preferably include an eccentric which are preferably substantially commonly oriented. The countershaft is coupled to a drive member such as the internal wire of a Bowden cable. The internal wire is remotely driven by a conventional motor. Typically, such motors will operate at 8,000–15,000 rpm.

In other embodiments, the applanator will be provided with grooves or a plurality of perforations to provide relieved areas which permit fluid to be channeled away from the blade and cornea. The perforations of the relieved areas will be positioned in proximity to the corneal surface of the eye to permit fluid to be drawn off, but of a size not to interfere with the cutting action of the blade. In the alternative, the underside of the applanator may be provided with a plurality of grooves providing a relieved area along which fluid may flow to the edges of the applanator. Furthermore, the applanator may be provided with a strain gauge for measuring the force of the eye against the applanator so that the surgeon may detect directly the intraocular pressure.

Therefore it is an object of the present invention to provide an improved microkeratome.

It is a further object of the present invention to provide an improved microkeratome which provides an improved cut of the eye resulting in a flap consisting of the outermost epithelium layer, the Bowman's layer, and the stroma leaving a hinge connecting the flap to the remainder of the eye.

It is a further object of the present invention to provide an improved microkeratome which provides an improved suction ring.

It is a further object of the present invention to provide an improved microkeratome which provides an improved suction ring which provides improved interocular pressure results.

It is a further object of the present invention to provide an improved microkeratome which provides an improved suction ring which allows for more accurate interocular pressure results.

It is a further object of the present invention to provide an improved microkeratome which provides an improved suction ring which allows for more accurate interocular pressure readings before, during, and after the cutting process.

It is a further object of the present invention to provide an improved microkeratome which includes an applanator plate which is adjustable in height relative to the aperture of the suction ring.

It is a further object of the present invention to provide an improved microkeratome which includes a hingedly removable applanator plate.

It is a further object of the present invention to provide an improved microkeratome which includes a thin blade in tension.

It is a further object of the present invention to provide an improved microkeratome which includes a moving shoe ahead of the cutting edge to provide clearance for the flap between the cutting edge and the applanator plate during the cutting process.

It is a further object of the present invention to provide an improved microkeratome which includes a simplified cable drive including a single core member.

It is a further object of the present invention to provide an improved microkeratome which includes a seismic drive to provide side-to-side cutting action of the blade along an axis parallel to its cutting edge.

It is a further object of the present invention to provide an improved microkeratome which can measure pressure at the applanator plate.

It is a further object of the present invention to provide an improved microkeratome which provides elastohydrodynamic entrapment relief.

It is thus an object of the present invention to provide an improved microkeratome involving a minimum of moving parts, a simplified oscillating drive, and a minimum weight.

It is another object of the present invention to provide an improved microkeratome which reduces film build-up beneath the applanator to provide cuts of a consistent thickness.

It is another object of the present invention to provide an improved microkeratome which can be useful in reducing the loss of the "cap" consisting of the epithelium and Bowman's membrane which is to be replaced during lamellar surgery.

It is a further object of the present invention to provide an improved microkeratome which allows for improved viewing of the cutting procedure as the cutting is being done.

Other objects, features, and advantages of the present invention will become apparent upon reading the following detailed description of the preferred embodiment of the invention when taken in conjunction with the drawing and the appended claims.

BRIEF DESCRIPTION OF THE DRAWINGS

FIG. 6 is an isolated bottom plan view of the base assembly 20.

FIG. 7A is a side partial cross sectional view of an eye in contact with a suction ring 22, prior to vacuum being applied.

FIG. 7B is a similar side partial cross sectional view of an eye in contact with a suction ring 22 after vacuum being applied and before the applanator plate has been brought into contact with the eye.

FIG. 14 is a more detailed front end view of a cutting blade assembly 70 mounted about an applanator plate 52, except that the cutting blade is not shown.

FIG. 15 is a view along line 15—15 of FIG. 14.

FIG. 33 is a side elevational view of an alternate base configuration 500, which includes an inclined upper holder 502, which is rigidly attached through the body of the alternate base configuration 500 relative to an integral suction ring 501. As reference surface 505 is provided on the left, and a slot 506 is provided on the right, which as described below will accept an applanator plate assembly through a left-to-right sliding motion. This configuration does not allow for height adjustment of the applanator plate.

FIG. 34 is a partial side partial cross-sectional view of an applanator assembly 510 according to an alternate configuration. This assembly 510 has a reference surface 515 and includes a holder 511, a latch 513 pivotably attached to the holder 511, and an applanator plate 512 rigidly attached to the holder 511. The latch 513 is configured to move to allow the applanator holder and applanator plate to be moved together into place, while release of the latch engages a portion of an associated base framework, such that the applanator is held in place relative to the base framework such as 500. The configuration of FIG. 34 may be used in conjunction with the configuration of FIG. 33, and as noted above a rigid configuration which does not allow adjustability of the plate is contemplated.

FIG. 35 is a top elevational view of the configuration shown in FIG. 33, with an aperture 503 shown, and the holder 502 shown. It may be understood that the edges or walls 507 of the base in this configuration may rise higher than earlier versions, to preclude the introduction of foreign materials which may tend to jam mechanisms working therein.

FIG. 36 is a illustrative view of an applanator assembly 520, having a reference surface which includes an adjustability feature. By height adjustment of an intermediate adjustment member 526 which holds the applanator 522, the applanator plate can be raised and lowered with respect to the main holder base 521.

FIG. 37 is a partial side illustrative view of a modular cable drive assembly 530, which includes the use a rotating sheath clamp 535, which is allowed to rotate relative to a camshaft mount 531, to remove rotation torque which the surgeon may feel when manipulating the device. As may be understood, longitudinal movement of the rotating sheath clamp 535 is restricted due to its intimate engagement with the camshaft mount 531, but it is allowed to rotate relative to the camshaft mount 531. Also shown is a cam shaft 537, a linear bearing 532, and a sheath cable including a sheath 538.

DETAILED DESCRIPTION

Figure 1:
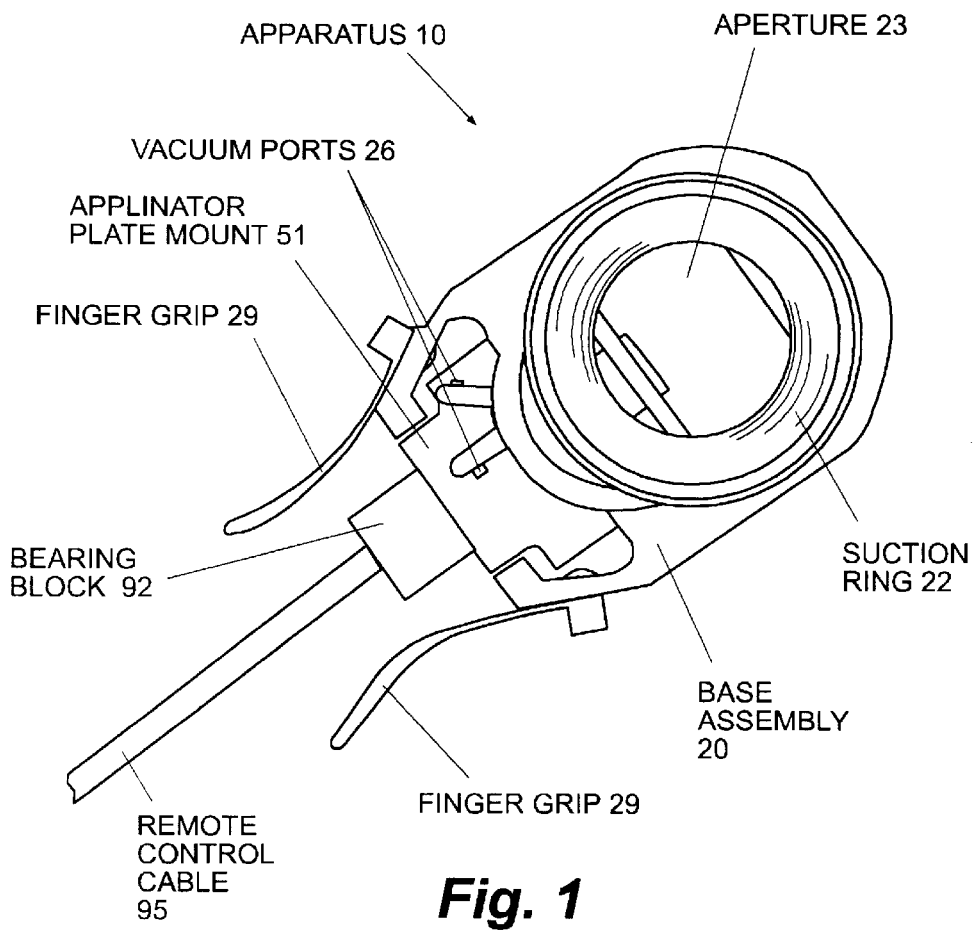
FIG. 1 is a bottom view of a microkeratome apparatus 10 in accordance with the present invention, with a remote control cable extending generally downwardly and leftwardly to the viewer.

The invention is now discussed in further detail in conjunction with the drawings in which like numerals designate like elements throughout the several views.

General Construction and Operation

In microkeratome 10 in accordance with the present invention generally includes a base assembly 20, with a finger grip 29 an applanator assembly 50, blade assembly 70, and a drive assembly 90. Other alternate mikrokeratome apparatuses will be discussed later in this application.

Figure 2:
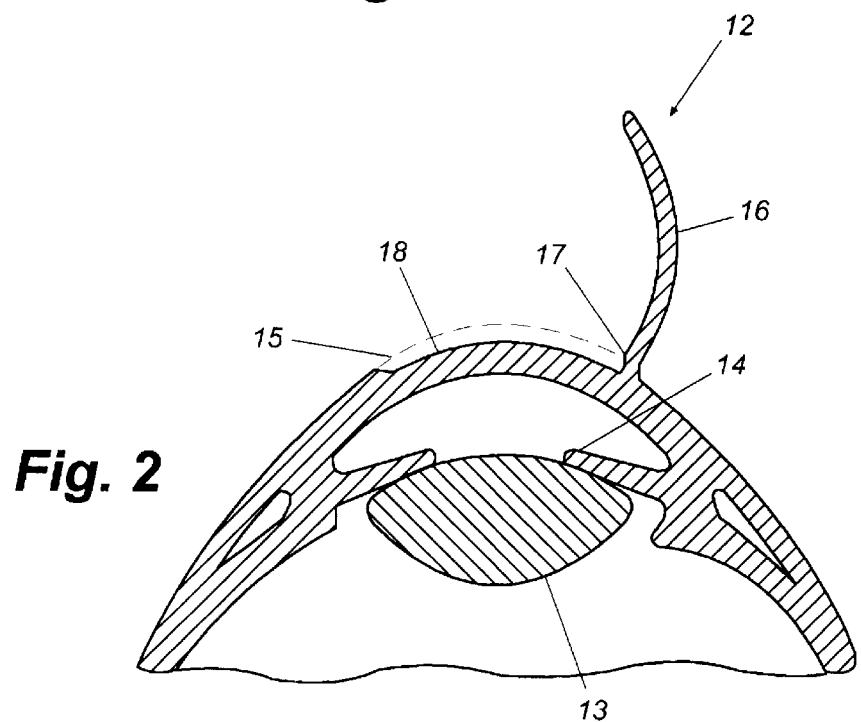
FIG. 2 is an enlarged fragmentary vertical cross-section view through an eye showing a flap cut in the cornea.
Figure 18:
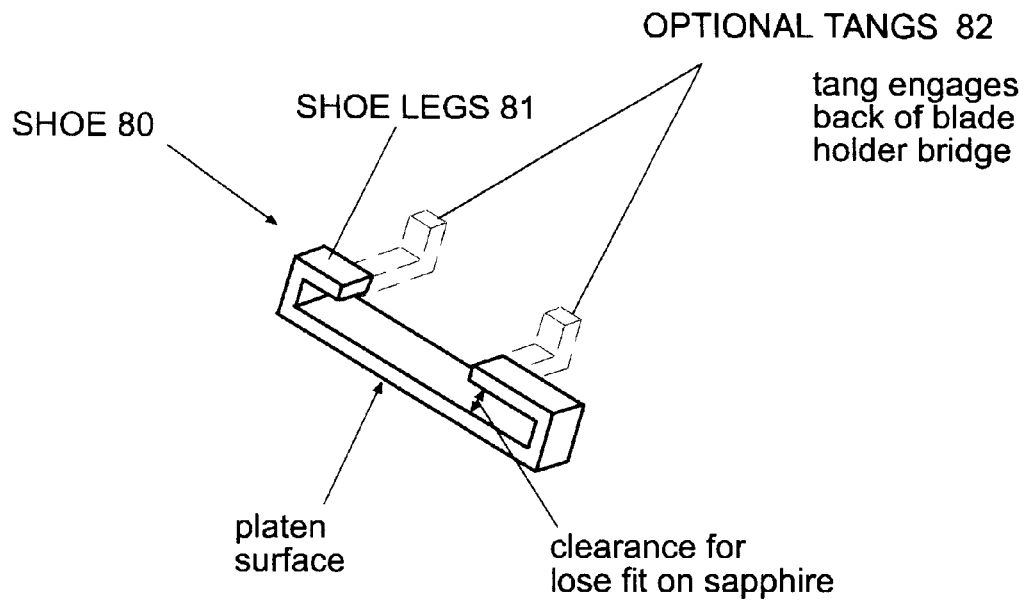
FIG. 18 is an isolated pictorial view of a shoe 80, with an alternate tang configuration shown in dotted line.

The microkeratome is useful in connection with surgery on the eye 12 shown in FIG. 18 which include a lens 13, iris 14 and cornea 15. Cornea 15 is typically about 550 microns thick. In accordance with the present invention, a flap 16 about 160–175 microns in thickness is cut from the cornea, the flap including the epithelium and Bowman layer, with the flap preferably being cut to a uniform thickness but remaining connected to the eye by a hinge 17. Lifting of the flap 16 as shown in FIG. 2 exposes the stromal bed 18 for ablation by an eximer laser or other suitable techniques.

The Base

Referring generally to FIGS. 3–5B, the base assembly 20 generally includes an integral suction ring 22, and includes a subassembly referenced as a release latch assembly 30. The general function of the base assembly 20 is to provide support for various other assemblies such as the blade assembly 70, the applanator assembly 50, and the oscillating/linear drive assembly 90. The body also includes finger grips 29 for holding the device with the fingers.

The body 21 of the base assembly 20 includes an integral suction ring 22. The suction ring 22 presents a circular aperture 23 into which the eye 12 is received during surgery, such that an eye can be placed under the applanator as discussed elsewhere. The suction ring 22 includes a base ring which rests against the patient's eye in sealing engagement.

Figure 8:
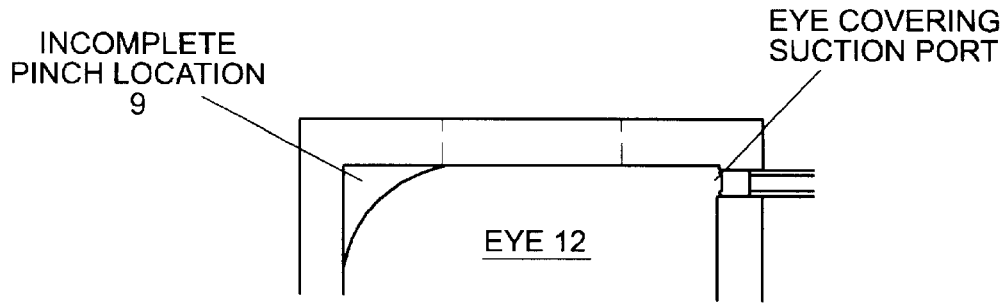
FIG. 8 is a side illustrative cross sectional view of a suction ring having discrete suction ports which evacuate air within the suction ring to cause the eye to be retained within the suction ring. As may be seen, in certain instances the eye be "sucked" into one or more of the ports, such as the one shown on the right, precluding adequate suction to reach other locations such as the incomplete pinch location 9 towards the left of FIG. 8.
Figure 9:
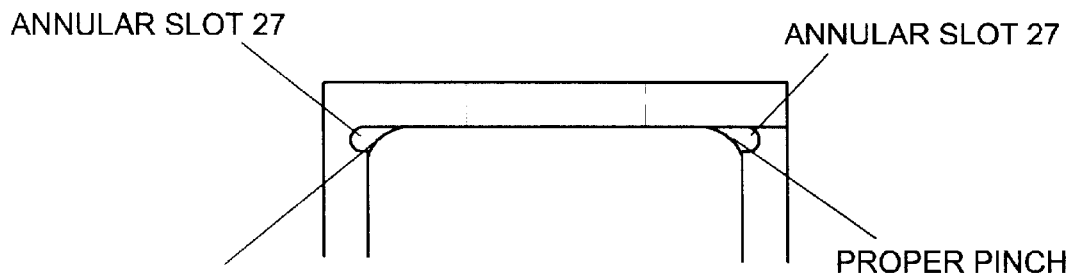
FIG. 9 is a side illustrative cross sectional view of a suction ring having an annular slot which tends to "distribute" the vacuum at locations throughout the suction ring internal periphery.

Within the suction ring 22 is defined an internal annular groove 27 which obviates the need for multiple vacuum ports. Reference is now briefly made to FIGS. 7A, 7B, 8 and 9. FIG. 7A is a side partial cross sectoinal view of an eye in contact with a suction ring 22, prior to vacuum being applied. FIG. 7B is a similar side partial cross sectional view of an eye in contact with a suction ring 22, after vacuum being applied and before the applanator plate has been brought into contact with the eye. It has been recognized by the applicants that the "pinching" of the eye 12 as shown in FIG. 7B is preferable, and that the intraocular pressure is increased, which correspondingly provides improved cutting characteristics. FIG. 8 is a side illustrative cross sectional view of a suction ring having discrete suction ports which evacuate air within the suction ring to cause the eye 12 to be retained within the suction ring. As may be seen, in certain instances the eye 12 can be "sucked" into a port, such as the one shown on the right, precluding adequate suction to reach other locations such as the incomplete pinch location 9 towards the left of FIG. 8. The present invention improves on that shown in FIG. 8 with the FIG. 9 version, which includes an annular slot which tends to "distribute" the vacuum at locations throughout the suction ring internal periphery, resulting in proper pinches such as designated as 8 in FIG. 9.

Referring back generally to FIGS. 3–5B, the suction ring 22 includes two vacuum ports 26 located within the annular groove, although other further vacuum ports may be utilized without departing from the spirit and scope of the present invention. One of these ports is connected to a conventional vacuum pump (not shown) to provide a partial vacuum between the suction ring 22 and the patient to draw the cornea upwardly into engagement with the applanator.

As discussed above, one of the suction ports 26 within the annular groove 27 is connected to a conventional vacuum pump (not shown). However, one novel feature of this microkeratome according to the present invention is that more than one port 26 is provided, so that vacuum level may be measured directly at the fixation point rather than within a console near to the vacuum source (not shown), by attaching the other port 26 to a vacuum measuring device (not shown).

On the forward end of the base, extending from the top, are mounting flanges 28 used for mounting a release latch assembly 30, being a subassembly of the base assembly 20. The release latch assembly 30 is configured to releasably retain the forward (show in drawing) edge of the applanator plate 52. As discussed in further detail elsewhere, the rearward edge of the applanator plate 52 is retained by the applanator plate mount 51, which is itself pivotally mounted relative to the base assembly 20.

The release latch assembly 30 includes two release latches 31 (two are used, although other further latches may also be used), which are rigidly attached to a release latch pin 32. The release latch assembly further includes a pair of end screws 33, a release trigger 34, a pair of springs 35, a rocker member 36, and a rocker member adjustment thumb screw 37. In the preferred embodiment, the release latch pin 32, release latches 30, and the release trigger 34 are all part of an integral unit.

A pair of end screws 33 rotatably pass through corresponding mounting flanges 28 (being part of the base assembly 20) and threadably engage the ends of the release latch pin 32, such that the release latch pin 32 and the release latches 31 are rotatably mounted relative to the base assembly along a pivot axis PA#1, which is substantially parallel to the X axis, and extends substantially along the central axis of the elongate release latch pin 32 which is not entirely circular in transverse cross section but includes various flat spots for clearance purposes.

The release latches 31 are configured to engage and retain the upper surface of the applanator plate 52 proximate its forward edge, in order to releasably retain the forward edge of the applanator plate 52 in a fixed but adjustable location. Spring force to provide such retention is provided by a pair of compression springs 35 intermediate the release latches 31 and the body 21 of the base assembly 20. However, the release latches 31 may be pivoted out of the way against such spring force by moving the release trigger 34 in a direction designated as R in FIG. 4. Such trigger movement may be used to release an applanator plate 52 to gain access to the cornea or to remove and replace the blade as described later. It may therefore be understood that the springs 35 bias the release latches 31 downwardly onto the forward edge of the applanator plate 52.

Figure 11:
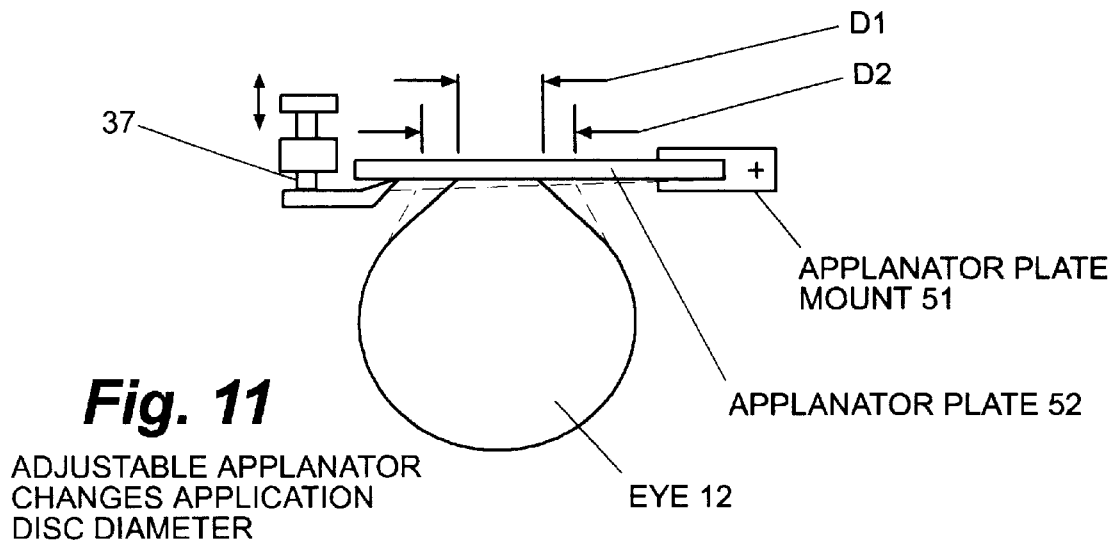
FIG. 11 is a side elevational isolated illustrative view of an eye in contact with the plate of an applanator assembly 50, with the height adjustment screw 37 adjustable up and down along its vertical longitudinal axis to provide different diameters D1, D2, for the applanation disc (the disc-shaped eye portion touching the applanation plate).

The applanator height adjustment thumb screw 37 is configured to adjust the height of the front edge of the applanator plate 52 relative to the base assembly 20. The advantage of such adjustment is shown in brief reference to FIG. 11, which is a side elevational isolated illustrative view of an eye 12 in contact with the plate of an applanator assembly 50, with the height adjustment screw 37 adjustable up and down along its vertical longitudinal axis to provide different diameters D1, D2, for the applanation disc (the disc-shaped eye portion touching the applanation plate).

Figure 3:
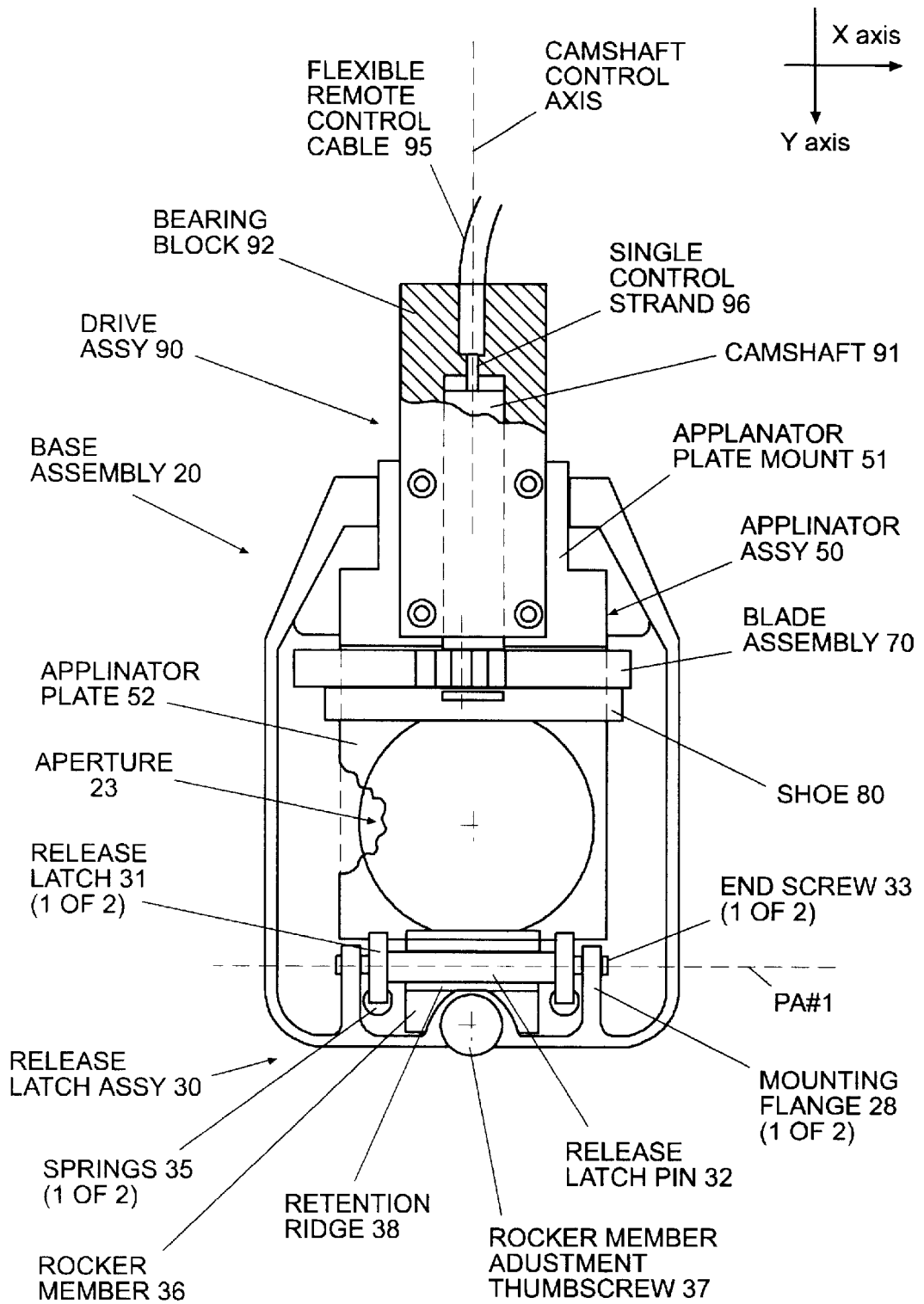
FIG. 3 is a top plan partial cross-sectional view of a microkeratome apparatus 10 in accordance with the present invention, showing a part of the applanator plate cut away to show the aperture without looking through the clear applanator.
Figure 4:
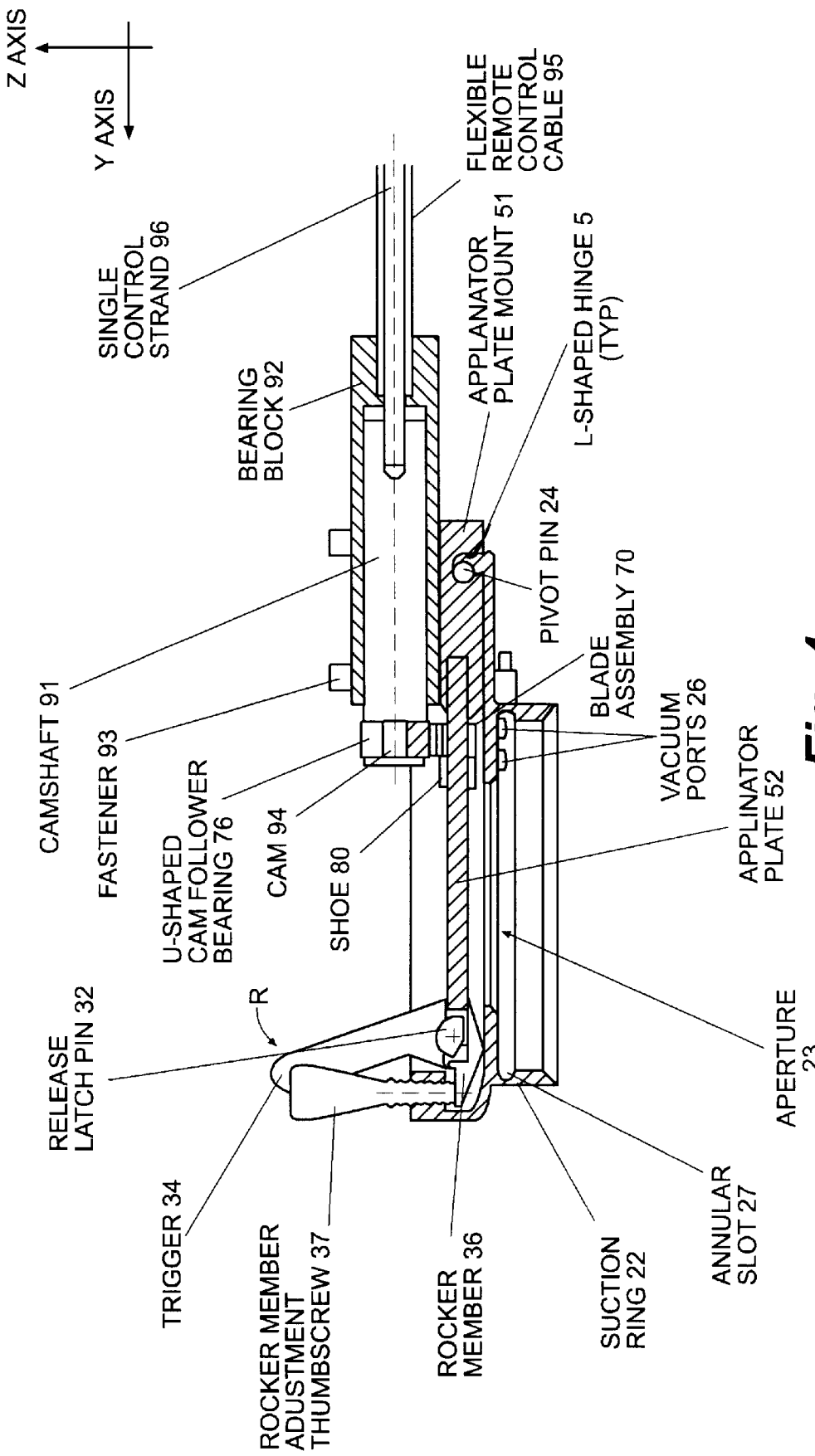
FIG. 4 is a side elevational partial cross-sectional view of the device of FIG. 3, with the cross sections taken essentially through the center of the device.

Referring now back to FIGS. 3–5B, and particularly to FIG. 4, upon rotation of the adjustment thumb screw 37, the rocker member 36 is pushed downwardly at its forward end, which due to the "see-saw" shape of the rocker member causes upward movement of its rearward end, which is positioned underneath the front edge of the applanator plate 52. Therefore, it may be understood that as the adjusting screw 37 is tightened downwardly as FIG. 4 is viewed, so is the forward end of the applanator plate 52 adjusted upwardly as FIG. 4 is viewed, against the downward force provided by the applanator release latches 31, which as noted above are themselves urged into their engaged position by the pair of biasing springs 35.

A retention ridge 38 (see FIG. 3) extending upwardly from the rocker member 36 serves to prevent the rocker member from falling into the aperture 23 when the latch assembly 30 is released and the rocker member is loose.

The Applanator Assembly

The applanator assembly 50 is pivotably as well as releasably attached relative to the base assembly 20, and generally includes an applanator plate mount 51, and an applanator plate 52 (a.k.a. applanation plate).

The applanator plate 52 is preferably made of clear sapphire and is about 0.042 inches thick. This transparency allows one to watch the cut proceed through the clear sapphire applanator. This can be an advantage in slow cutting systems in that the cut can be stopped if it appears that damage is being done. The applanator plate 52 is substantially rigidly attached to the applanator plate mount 51.

The applanator plate 52 is hinged relative to the base assembly 20 about an axis substantially parallel to the "X" axis. The entire applanator assembly 50 is mounted such that it can pivot relative to the sidewardly extending pivot pins 24 extending from the body 21 of the base assembly 20, but if it is pivoted to a certain degree, it can be removed. This is done by providing the applanator plate mount 51 with L-shaped hinge slots 53, which allows the applanator assembly 50 to pivot throughout a particular range about the opposing pins 24, but when rotation has reached a certain degree the applanator assembly 50 can then be removed by allowing the pin to slide out of the slots 53.

The applanator plate mount is further configured to support the bearing block 92 of the oscillating drive assembly 90, by use of fasteners 93 as discussed elsewhere. Therefore it should be understood that as the applanator assembly 50 is pivoted upwardly and away from the base assembly 20, the bearing block assembly and the remainder of the drive assembly 90 (including the remote control cable 95) likewise can be removed, to allow access for the surgeon.

The Blade Assembly

The blade assembly 70 generally includes a blade holder body 71, a blade 75 held within the blade holder 70 and a U-shaped cam-following bearing 76 configured to accept a cam member 94 of a camshaft 91 from the drive assembly as discussed elsewhere. A discussed in detail below, the camshaft 91 drives the blade assembly in side-to-side oscillation along the X axis (which is parallel to the cutting edge of the blade 75), and also pushes the blade generally parallel to the "Y" axis to separate the flap from the eye.

Figure 12:
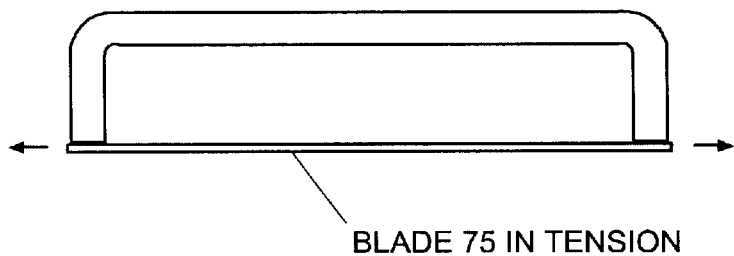
FIG. 12 shows the concept of using a "bow"-like configuration to provide a cutting blade 75 in tension, such that a thinner cutting blade may used.
Figure 13:
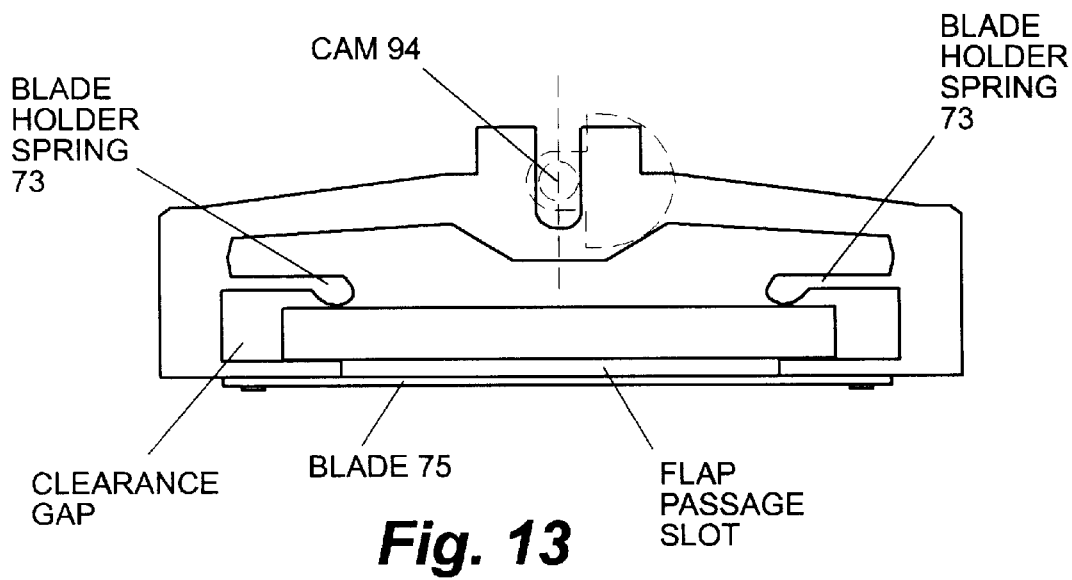
FIG. 13 is a front end view of a cutting blade assembly 70 mounted about an applanator plate, showing the slot through which the cut eye flap may pass during the cutting process. Also shown in dotted line is an alternate seismic drive element shown in more detail in later drawings.

The blade holder body 71 includes a pair of side legs 72, a pair of blade holder springs 73, and a pair of mounting flanges 74, which as noted below act as "spacers". The blade 75 is held in tension between the mounting flanges 74 extending from the side legs 72. In one preferred embodiment, the blade is welded to the spacer mounting flanges, although other attachment possibilities are contemplated without departing from the spirit and scope of the present invention. The blade itself is preferably thin and narrow, as a thin blade displaces less corneal tissue in dissection. The same rigidity as a thick blade is achieved by placing the blade in tension as generally illustrated in FIG. 12 though the provision of a "bow"-shaped holder structure.

Figure 17:
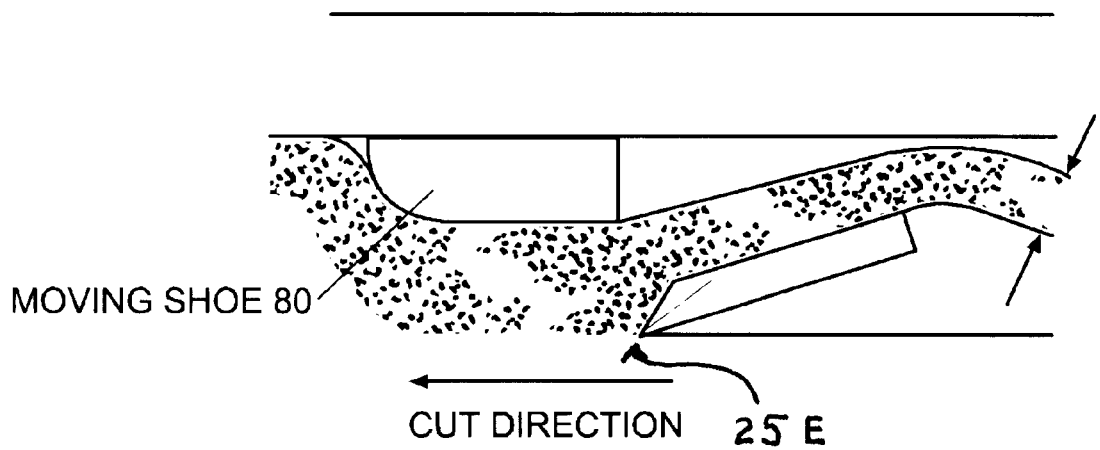

The blade 25 extends laterally beneath the applanator plate 52 and is preferably provided with a chisel-shaped cutting edge 25E having its lower edge leading the upper edge and thus angled downwardy and to the left as viewed in FIG. 17. This chisel-shaped orientation helps in engaging the cornea during the cutting of the flap. In the preferred embodiment hereof, the blade is preferably provided of stainless steel of a thickness of about 0.001 to about 0.004 inches thick and is about 0.035 to 0.09 inches wide.

The blade 75, being fixed within the blade holder, is constrained such that its cutting edge is constrained to move in a plane parallel to the primary planar surfaces of the applanator plate and at a fixed distance from the applanator. This distance defines the dissection depth (flap thickness), although this distance is not necessarily the same as the dissection depth, due to the existence of a shoe 80 leading the cutting edge as described later. The blade assembly has a pair of blade holder springs 73 which engage the top surface of the applanator plate 52 proximate its side edges, keeping the blade assembly in upwardly biased contact with the underside of the applanator plate to provide accurate cutting.

Figure 5A:
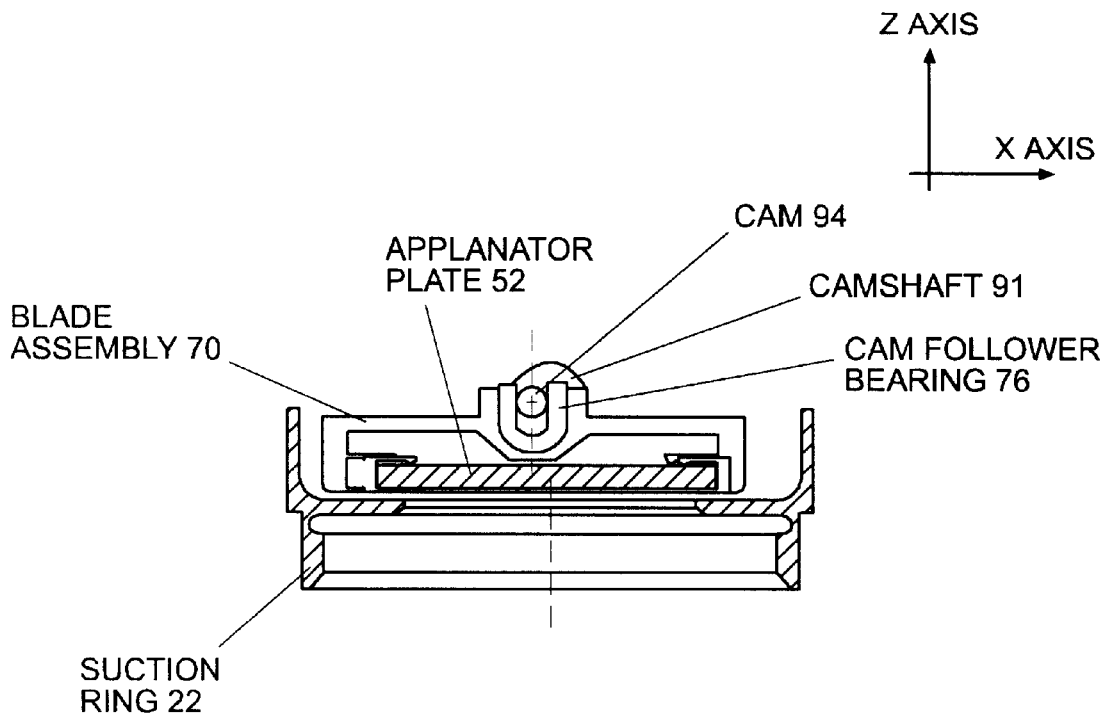
FIGS. 5A and 5B are front end sequential views of the device of FIG. 3, showing the side-to-side motion provided by the camshaft to the blade assembly.
Figure 5B:
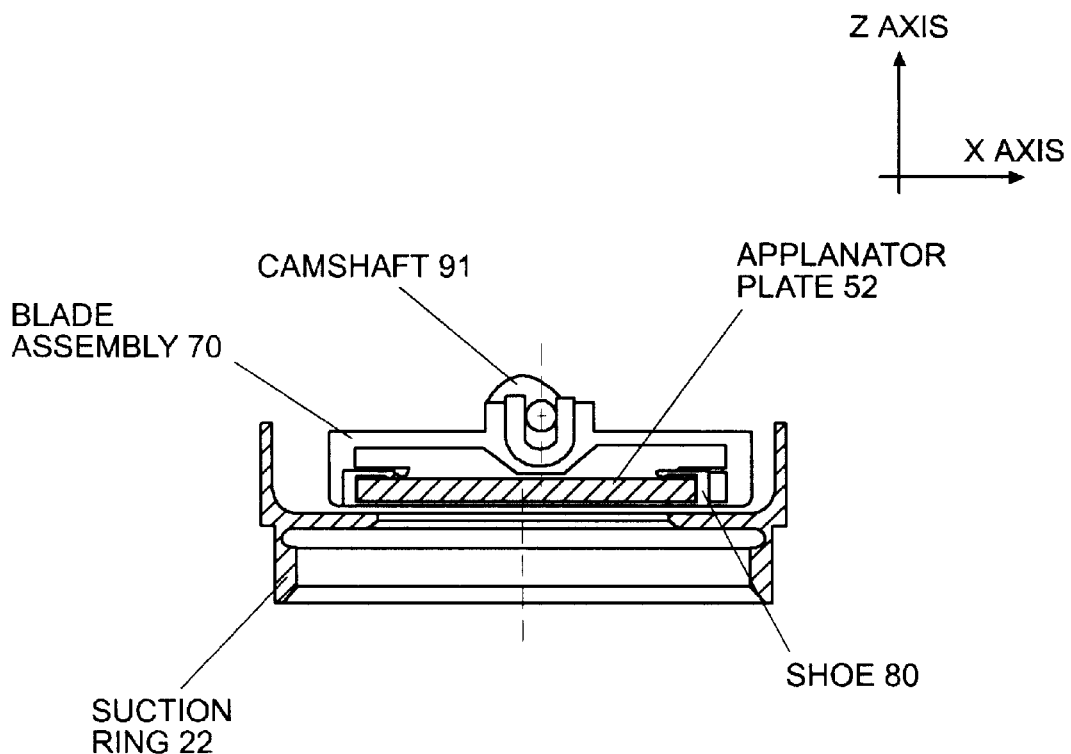

As shown in FIGS. 5A–B, clearance between the applanator plate 52 and the blade assembly 70 is provided to allow the blade assembly 70 to be moved side-to-side when so moved by the oscillating drive assembly 90.

The Shoe

Figure 16:
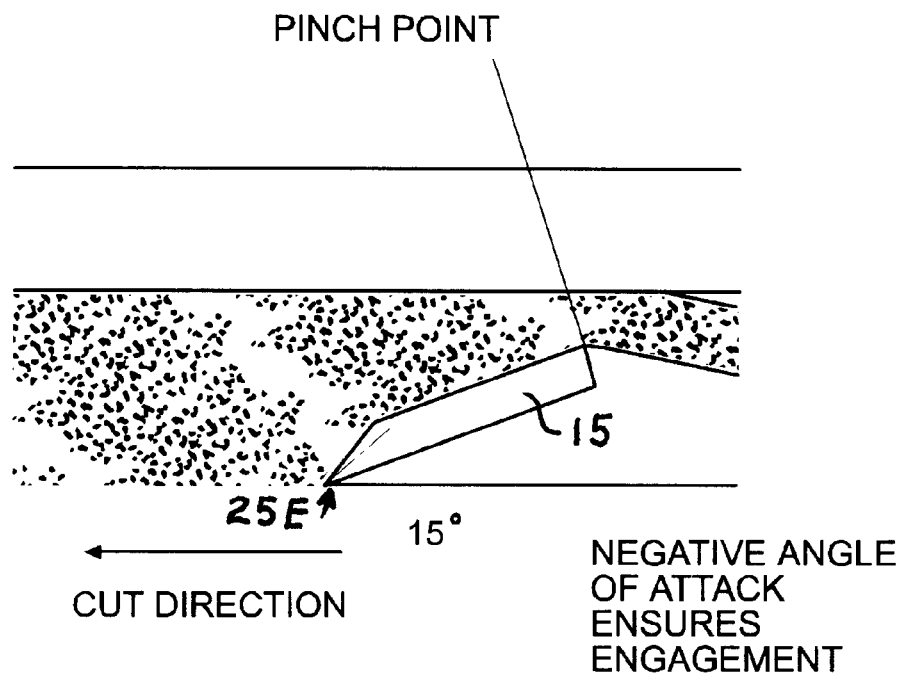
FIGS. 16 and 17 are side illustrative views showing left-to-right cutting actions of a blade, illustrating the use of a shoe 80 leading the cutting blade of FIG. 17, and the difference in the cutting action provided thereby.

The shoe 80 is configured to be slidably mounted onto the applanator plate 52 such that it can be pushed in front of the blade cutting edge as shown in FIG. 17, to prevent the undesirable pinching effect shown in FIG. 16. The shoe is not configured to move side-to-side as does the blade assembly.

The shoe 80 includes a pair of shoe legs 81, and a pair of shoe optional retention tangs 82.

Figure 10:
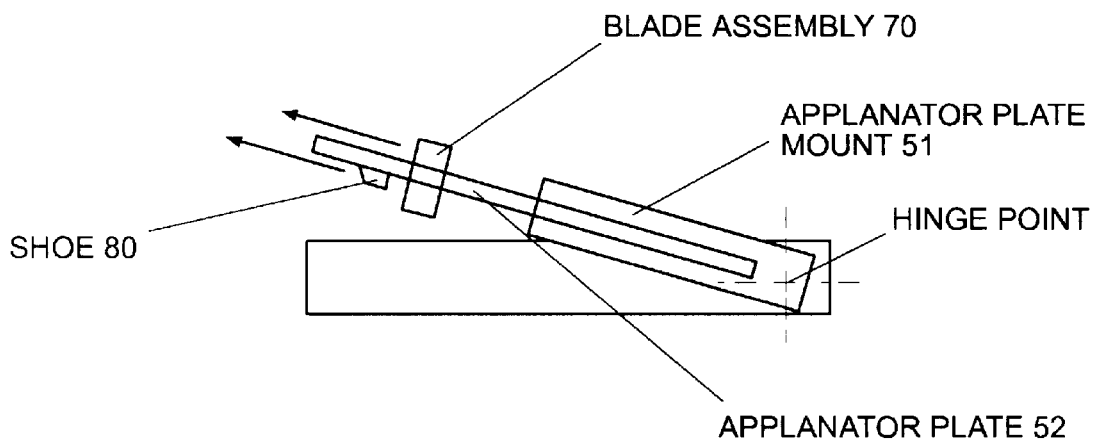
FIG. 10 is a side illustrative view showing the pivoting nature of the blade assembly 70 relative to the base assembly 20.
Figure 19:
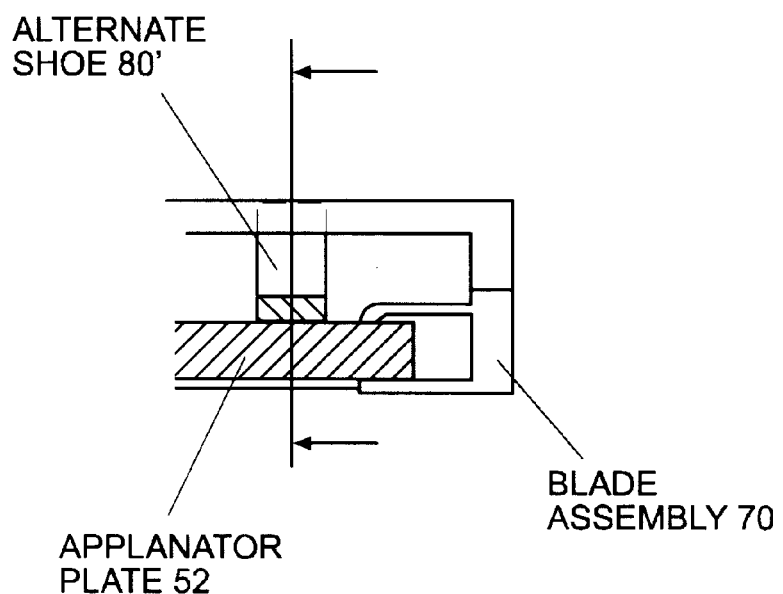
FIGS. 19 and 20 are partial front and side views, respectively, of a blade assembly 70 and alternate shoe configuration 80' (the one with the tangs) in engagement about an applanator plate 52.
Figure 20:
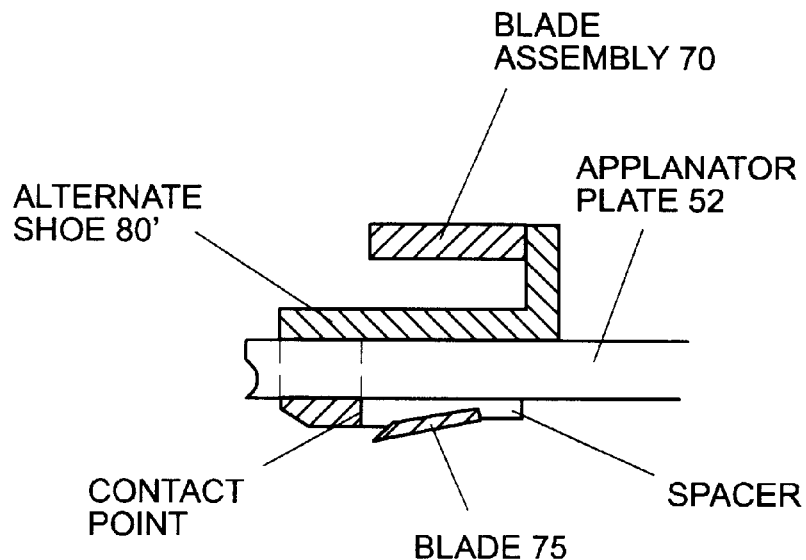

In a second embodiment, alternate of the shoe 80', shown in dotted line in FIG. 18 and in solid line shown in FIGS. 19 and 20, the shoe includes a pair of retention tangs 82 which allow the shoe to be retained by the blade assembly. Unlike the first shoe embodiment, this second shown configuration cannot be separately slid on and off the applanator plate 52 independently of the blade assembly 70 as shown in FIG. 10; instead the two members must be preassembled (by passing the tangs through the rectangular opening above the blade in the blade assembly) prior to being slid on the applanator plate 52.

The Oscillating Drive

Referring again generally to FIGS. 3–5B, the oscillating drive assembly 90 is mounted to the top of the applanator plate holder 51 and provides two types of motion to the blade assembly 70, including the blade 75. The first type of motion is side-to-side oscillation along the X axis, which is parallel to the cutting edge of the blade 75, to assist the cutting process. The second type of motion is longitudinal motion perpendicular to the cutting edge of the blade and generally parallel to the "Y" axis, to advance the cut along the cornea.

Figure 21:
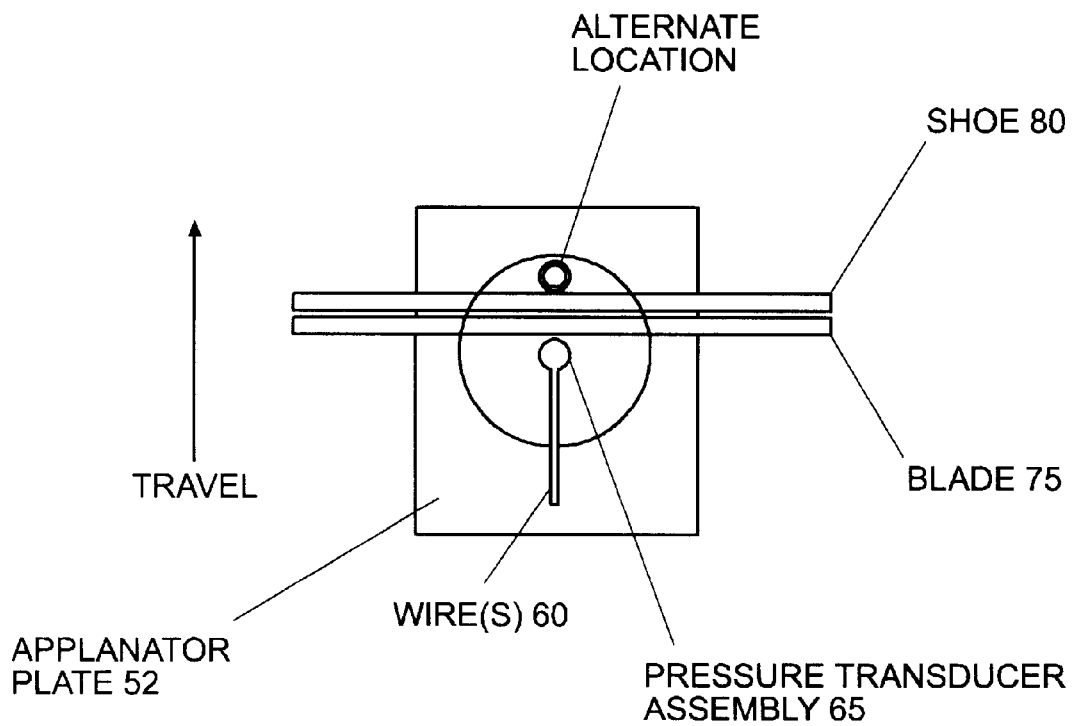
FIG. 21 is a top plan view of an applanator plate 52, showing a pressure transducer assembly 60 installed therein, and also showing a shoe 80 and blade 75 moving upwardly during the cutting process.

The first type of motion is illustrated in reference to FIGS. 5A–B; the second type of motion is generally shown in FIG. 21, 16 and 17.

Referring back to FIGS. 3–5B, the bearing block 92 includes an internal elongate bore configured to accept a length of the cam shaft 91, allowing for rotational and linear movement of the camshaft 91 within the bore of the bearing block 92, which translates into the aforementioned side-to-side and longitudinal motion, respectively, of the blade assembly 70. The camshaft 91 rotates about an axis substantially parallel to the "Y" axis, and moves longitudinally along an axis substantially parallel to the "Y" axis when the cut is being made. This movement is caused by similar movement of the single internal strand 96 (which can be a solid wire or could be a bundle of smaller wires) within the outer sheath of the flexible control cable 95, which is driven by a remotely located electric drive motor discussed later.

As noted above, the bearing block 35 is configured to be mounted atop the applanator plate mount by bearing block fasteners 36. Therefore, as the applanator assembly 50 is pivoted upwardly and away from the base assembly 20, the bearing block 92 and the remainder of the drive assembly 90 likewise is moved out of the way, as the bearing block 92 is attached to the applanator plate mount 51.

IOP Sensor

Figure 22:
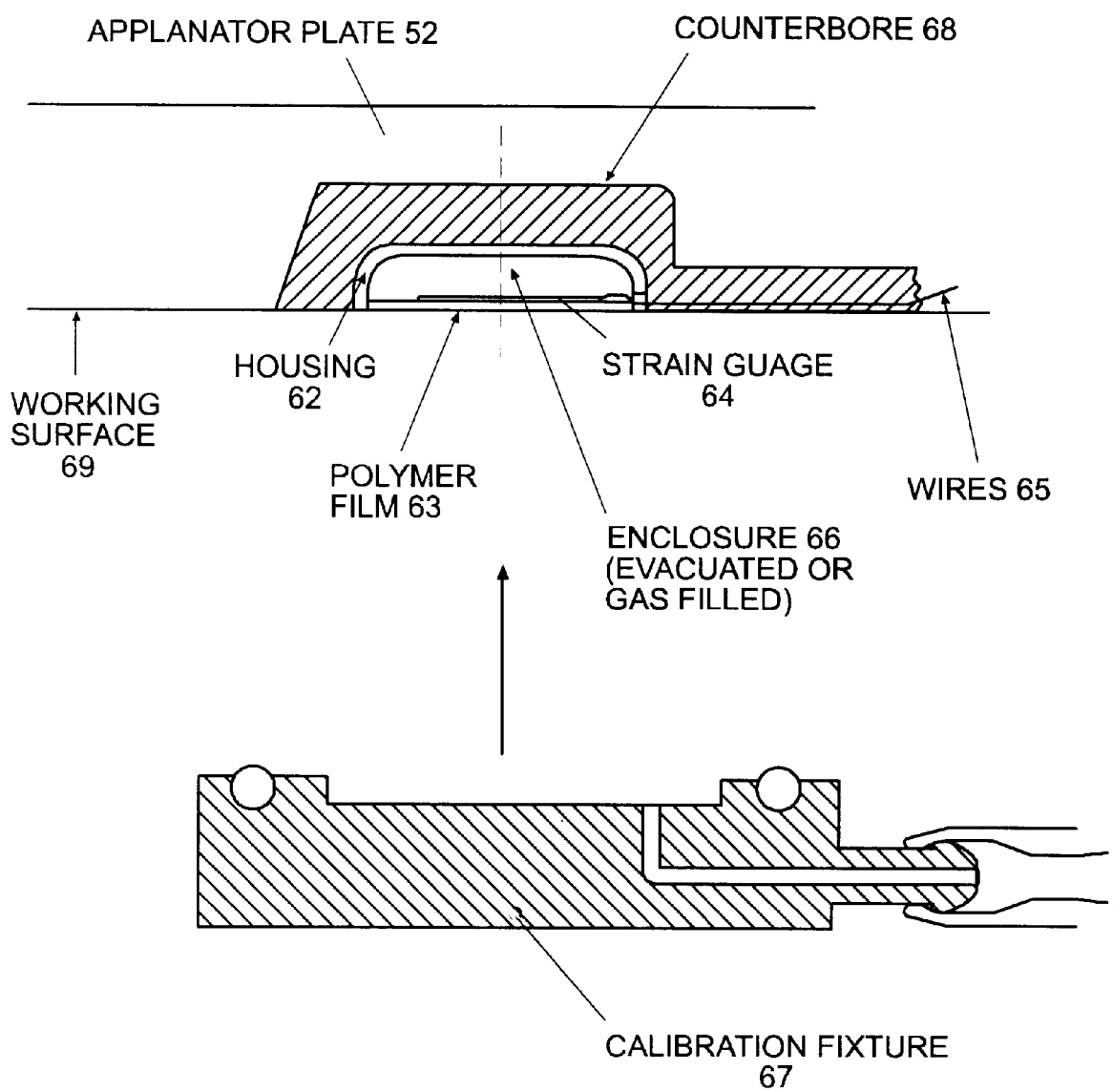
FIG. 22 is a more detailed side partial cross-sectional view of an interocular pressure transducer assembly 60 installed within an applanator plate 52.

Reference is now made FIGS. 21 and 22 to discuss an interocular pressure ("I.O.P") sensor transducer assembly 60 which can be mounted within the applanator plate 52. A counterbore 68 is first provided perpendicularly into the primary planar surface of the applanator surface which will come into contact with the eye (a.k.a. the "working surface" 69). An filler 61 such as silicone is used to support a dish3 shaped metal housing 62 which opens in the same direction as does the counterbore. The opening of the dish-shaped metal housing 62 is covered by a polymer film 63 which allows a strain gauge 64 to be mounted on the back side of the polymer film 63 while enclosed within an enclosure 66 defined by the housing 62 and the polymer film 63. The enclosure 66 can be evacuated or gas filled. One or more wires 65 lead from the strain gauge 64 to suitable meters. The stain guage can be calibrated by a calibration fixture such as 67 and pressure readings at the working surface 69 can be determined to determine IOP.

Drive Motor

Figure 30:
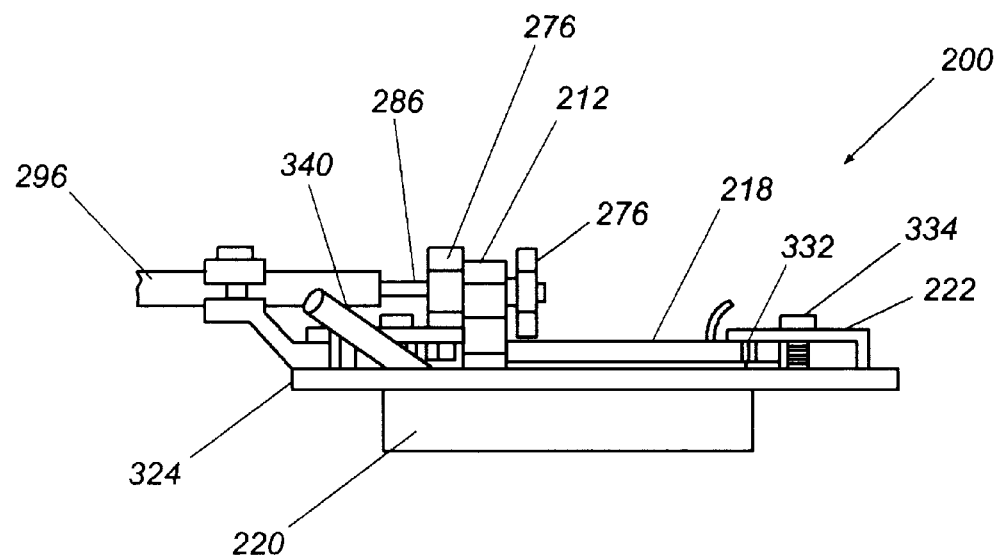
FIG. 30 is a side elevational view of the microkeratome 200, showing the drive wire of the Bowden cable connected to the countershaft provided with the eccentric weight thereon.

A motor which can be used in conjunction with the apparatus 10 according to the present invention is shown in FIG. 30 as being used with another embodiment. Details of this motor can be referenced later, but generally described the motor is of conventional configuration for operating at 8,000–15,000 rpm, and may be manually shifted toward and away relative to the suction ring to move the blade longitudinally to cut the flap. It may be understood that rather than manual operation, suitable actuators may be coupled with motor to electronically control travel of the blade during cutting of the flap.

Adjustments

As noted above, the applanator plate can be raised and lowered with respect to the eye so that the applanation diameter is adjustable from 8.5–9.9 mm. The movement of the applanator is accomplished by the thumb-screw type arrangement described above.

Detailed Method of Operation

In operation, the shoe 80 and the cutting blade assembly 70/drive assembly 90 combination are slid onto the applanator plate 52. The applanator plate assembly 50 is then attached to the base assembly 20, and locked into place by use of the release latch assembly 30. The suction ring 22 is then placed over the patient's eye and suction applied to bring the cornea up into engagement with the underside of the applanator plate 52. Adjustments to the thumbscrew 36 can then be made. The cut can then be made.

The surgeon then initiates rotation of the motor to cause the drive assembly to provide side-to-side oscillation of the blade assembly 70 limited by combined clearances totaling approximately one millimeter. It may be appreciated that the rotation of the drive cable 95 at approximately 8,000–15,000 rpms produces a corresponding rate of oscillation of the blade.

The surgeon then operates a linear actuator such as known in the art, essentially moving the motor on a plate, causing thrust to be imparted to the blade assembly 70, causing it to slide longitudinally along axis Y of FIG. 3. As the blade is positioned approximately 180 microns beneath the shoe, a flap 16 of corresponding thickness is cut in the cornea 15 as the surgeon advances the blade.

In the human eye, the distance of longitudinal travel will typically be about 9 mm to cut a flap 16 of the desired configuration, leaving hinge 17. After the flap is cut, the surgeon retracts the blade assembly 70. Thereafter, the motor may be de-energized, suction discontinued to suction tube, and the suction ring removed to permit ablation of the stromal bed thus exposed by an eximer laser or other technique.

Alternatives

Reference is now generally made to FIGS. 27–31, for a description of a second microkeratome 200 embodiment.

In this configuration a suction ring of conventional configuration can be used, such as, for example, an Automated Corneal Shaper by Chiron, Inc. The suction ring 220 can be part of a base 324 presenting two longitudinally extending recessed slots 326 oriented along the side edges of the applanator 218.

Figure 31:
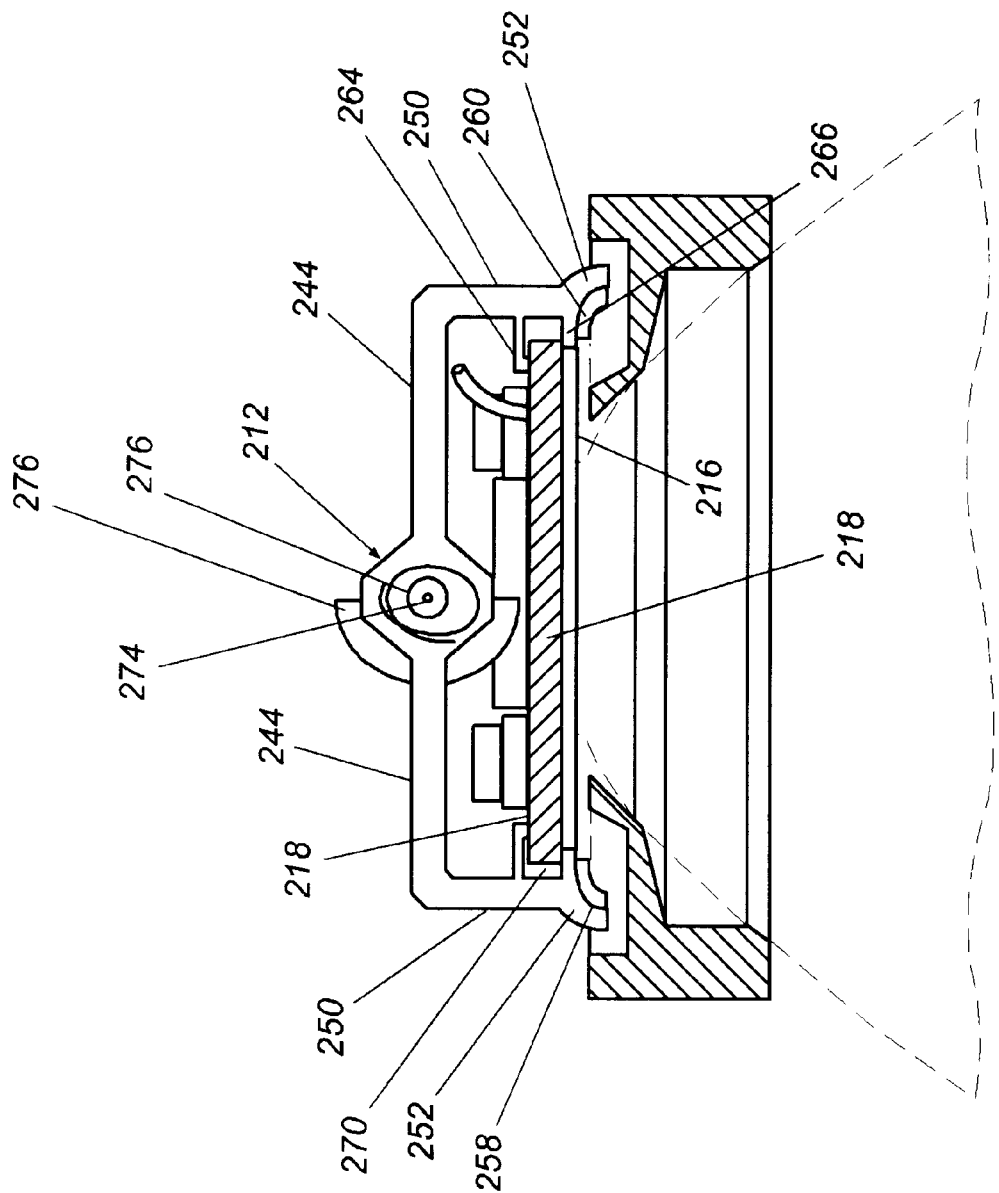
FIG. 31 is a rear end partial cross-sectional partial view of the microkeratome 200.
Figure 32:
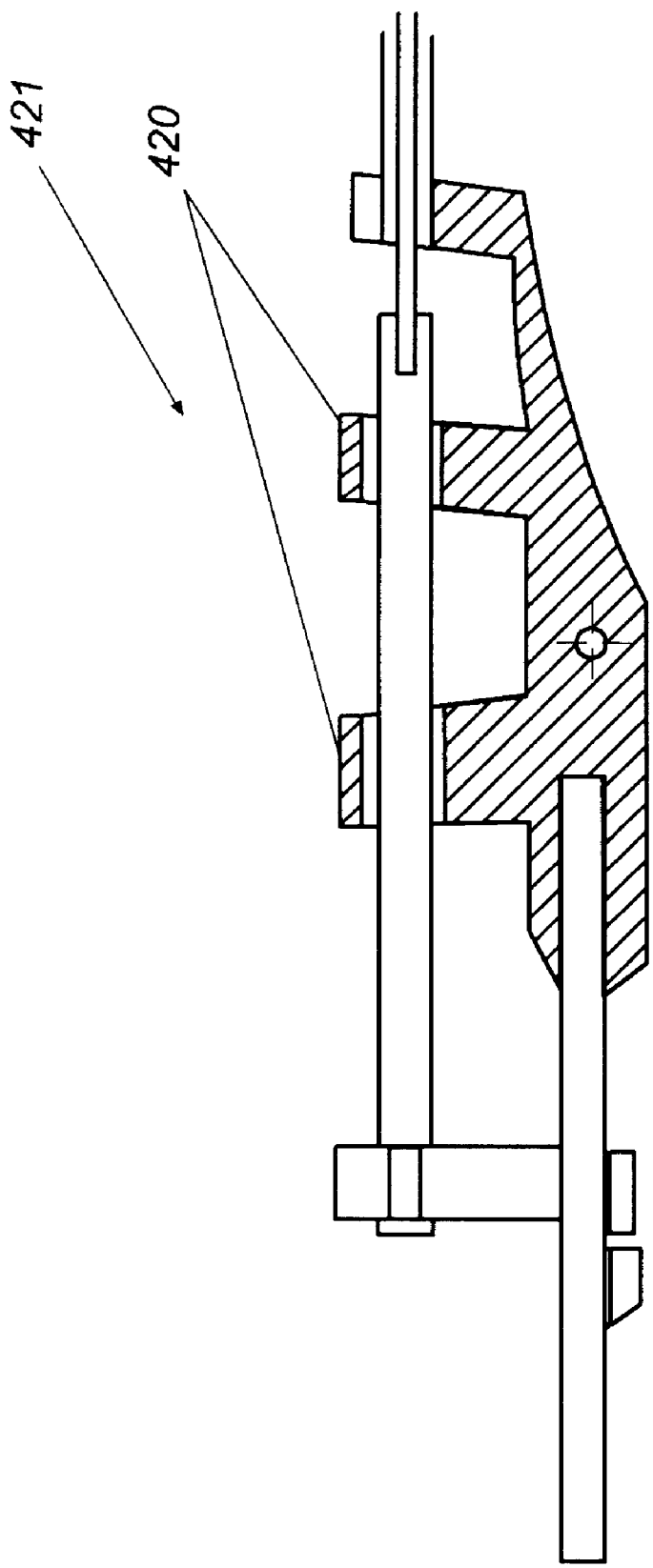
FIG. 32 is a side view of an alternate cutting blade assembly 420 including two spaced-apart bushings 421 used instead of the single plastic bearing block described earlier.

A cutting blade assembly 212 includes a centrally located body 240 presenting a central opening 242 (see FIG. 31). A pair of arms 244 extend laterally and on opposite sides from the body 240 and present respective legs 250 depending downwardly therefrom. Each of the legs terminate in lowermost respective feet 252, the feet being provided with threaded holes for receiving therein clamping screws 258 (see FIG. 31). The screws 258 threadably connect blade mounts 260 to their respective feet 252, blade 216 being positioned between screws 258 on each foot 252 and held in tension therebetween. Each leg 250 also presents inwardly oriented upper applanator spring clamp 264 and relatively rigid lower applanator shelf 266 for receiving applanator 218 therebetween. Placement of the applanator 218 between upper applanator clamp 264 and shelf 266 biases the clamp 264 upwardly, whereby the applanator is secured therebetween.

The combined magnitude of the side clearances 270 will be approximately 1 mm, thereby defining the oscillation travel of the blade assembly relative to the applanator plate as described above.

Four cleats 222 hold the applanator 218 securely in position on the base 324. Base 324 includes threaded holes for receiving screws 334 therein. As may be seen in FIG. 31, feet 252 and blade mounts 260 extend into tracks 326 respectively but are not engaged therewith because the clamp 264 and shelf 266 couple the frame 212 to the applanator 218 without permitting such engagement.

Figure 23:
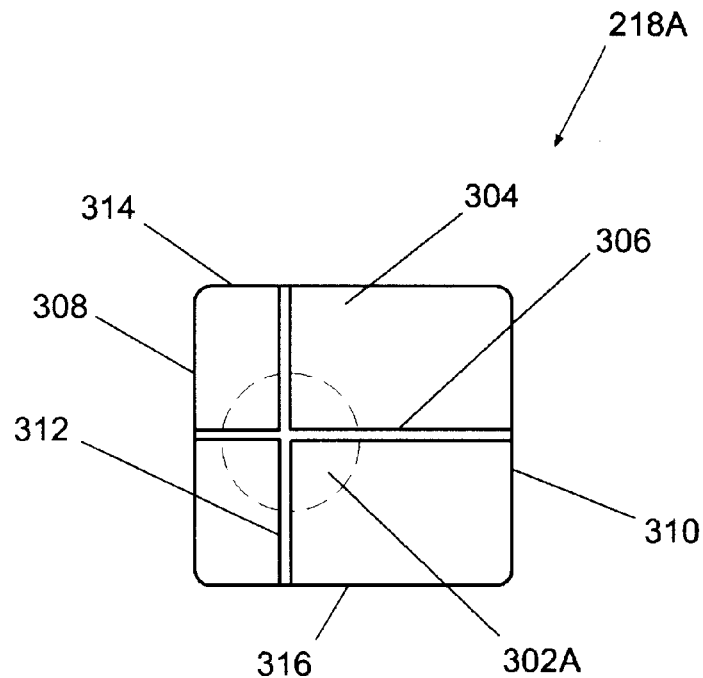
FIG. 23 is an isolated plan view of a first alternate applanator plate configuration 218A, which includes two crossing slots in the working surface, slots 306 and 312, which cross at about the location at which the eye is centered when contacted. The slots are approximately 0.002" wide, and 0.002 deep including a 0.001 bottom radius.

In another embodiment of the applanator 218*a* shown in FIG. 23, a relieved area 302 is provided on the underside 304 of the applanator by the provision of a longitudinally oriented channel 306 extending between the front edge 308 and rear edge 310 of the applanator and a lateral channel 312 extending between the side edges 314, 316 of the applanator 218.

Figure 24:
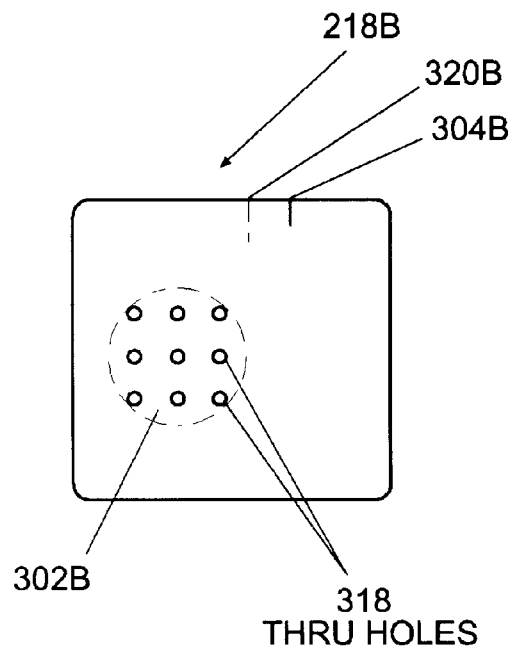
FIG. 24 is an isolated plan view of a second alternate applanator plate configuration 218 B, including a plurality of through holes 318, each approximately 0.004" in diameter.

Alternatively, as shown in FIG. 24, rather than having the relieved areas oriented for discharging fluid to the edges of the applanator, the relieved area 302*b* in applanator 218*b* may be provided by one or a plurality of perforations 318 extending between the underside 304*b* of the applanator to the top side 320*b* of the applanator to permit vertical passage of fluid entrapped beneath the applanator.

An alternate drive configuration is also shown in FIGS. 27–31 which includes the use of an eccentric or "seismic" drive rotatably driven by a motor 224 remotely located from the suction ring. Essentially, the seismic drive concept includes the use of one or more eccentrically-weighted weights 276 which, when rotated, cause the knife assembly to move side-to-side. An applanator 218 is situated to be supported by end supports such as, 332 to thereby permit the passage of the blade 216 beneath the applanator 218.

An eccentric drive includes a countershaft assembly which includes a shaft 274 (see FIG. 31) extending through the bore opening of the blade assembly 212 and a pair of eccentric weights 276 on each end of the relatively short shaft. The countershafts are most preferably provided of a tungsten/copper alloy of about 72% tungsten and 28% copper. The shaft 274 has one end attached to the drive cable 286 and is driven thereby.

Figure 27:
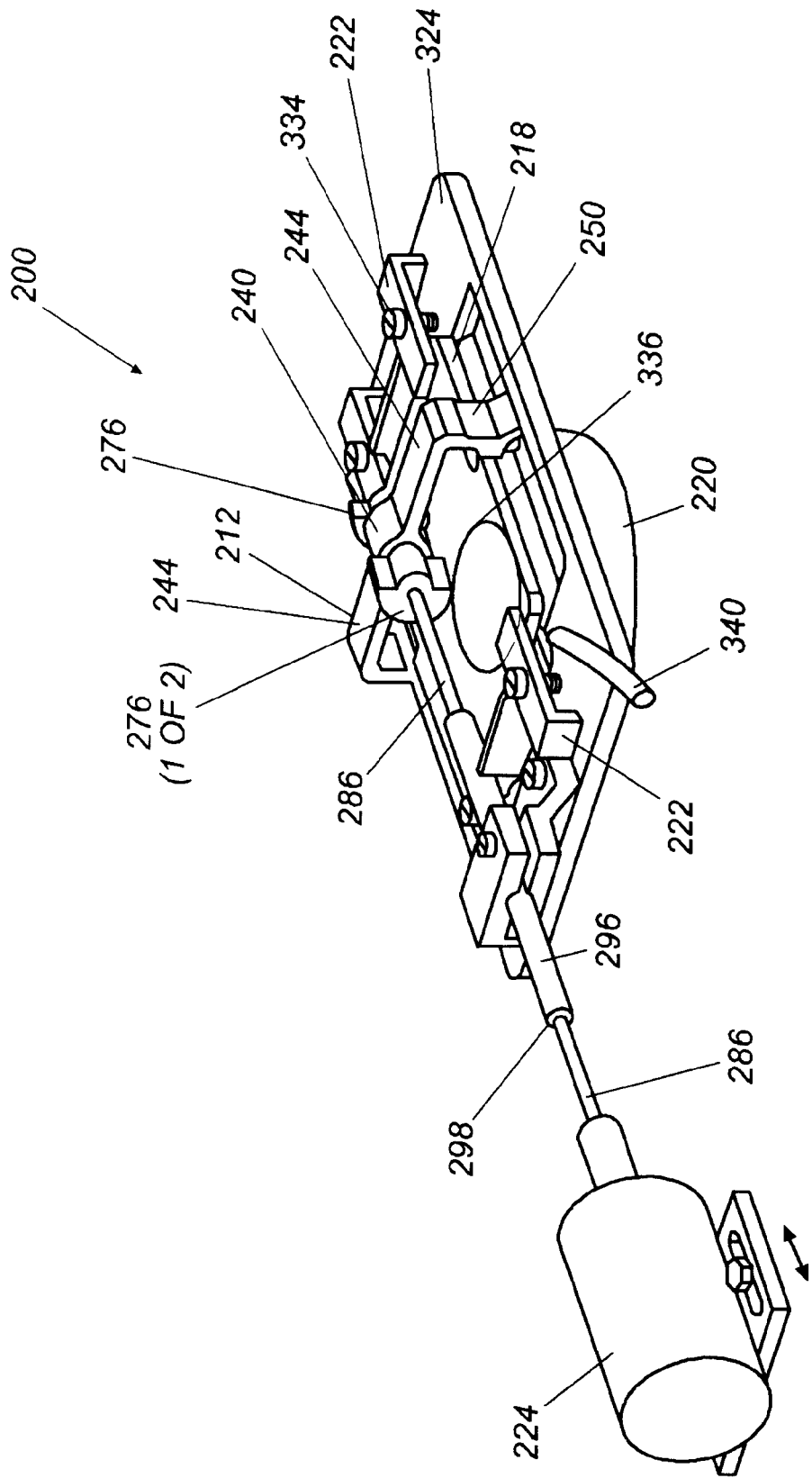
FIG. 27 is a pictorial view of a second microkeratome apparatus 200 according to the present invention.
Figure 28:
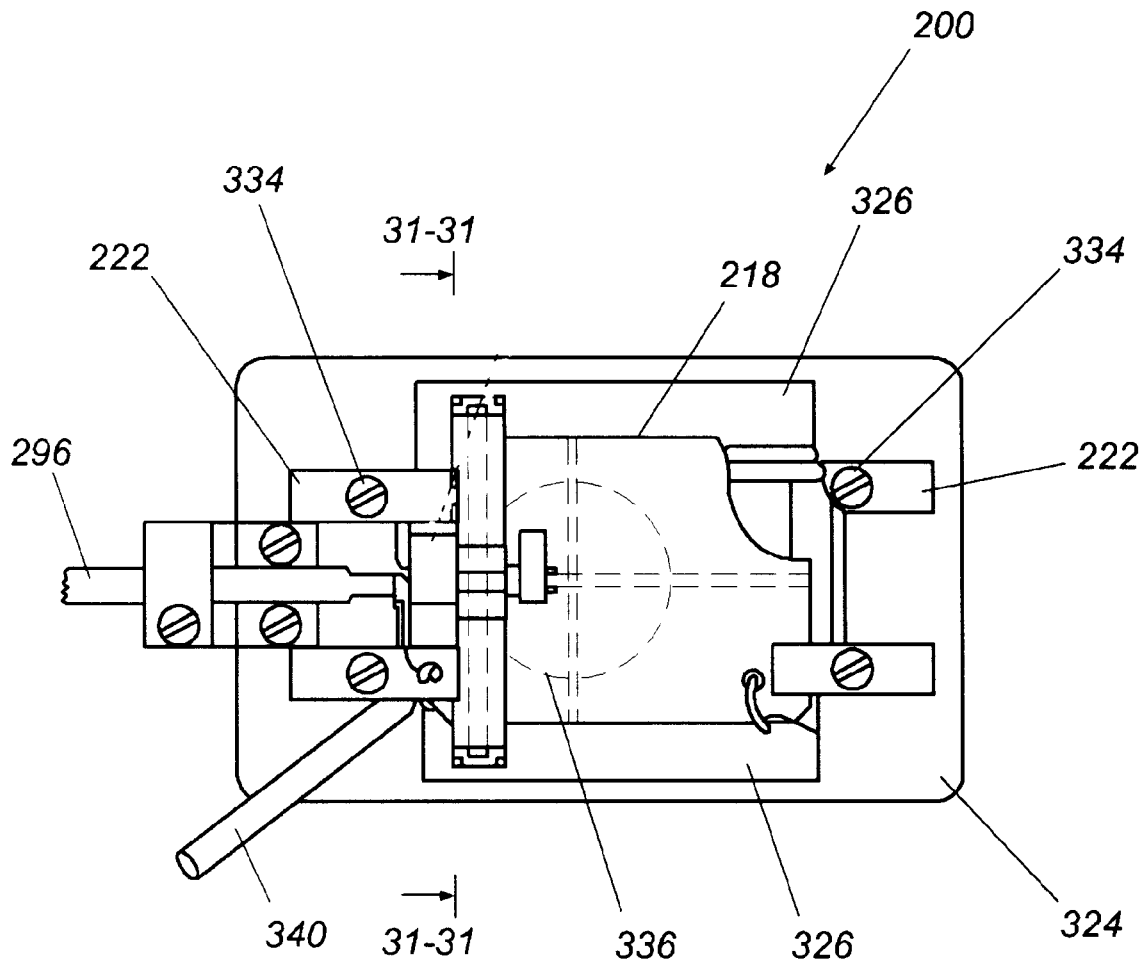
FIG. 28 is a top plan view of the microkeratome 200 hereof, with a portion of the applanator and the securing cleat removed to show the underlying structure of the suction ring.
Figure 29:
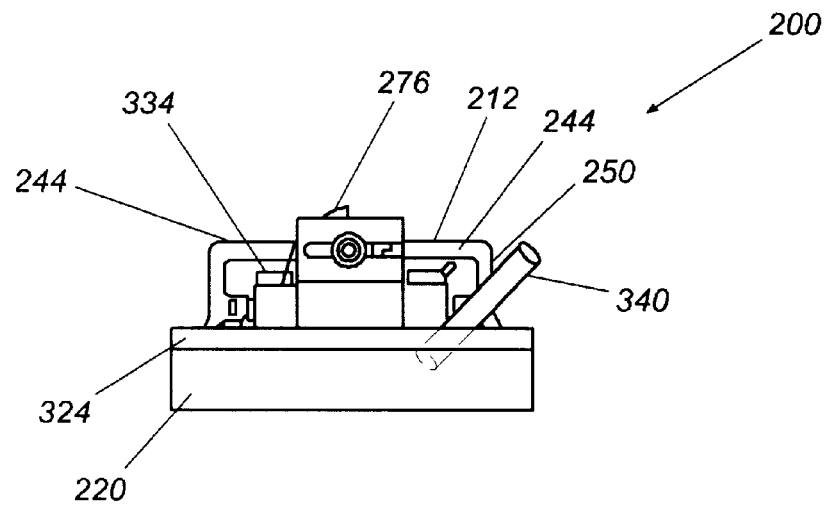
FIG. 29 is a rear elevational view of the microkeratome of FIG. 27 showing the suction ring, applanator and oscillating frame, with a portion of the suction tube shown in phantom.

Referring now to FIG. 27, the eccentric drive assembly is driven by a Bowden cable 296 including sheath 298 and drive cable 286. Drive cable 286 is longitudinally and rotatably moveable within sheath 298, and is coupled to motor 224. The sheath 298 is clamped relative to the overall assembly 200.

The blade and blade holder oscillate sidewardly with a stroke of approximately 0.9 mm and a rate equal to that of the eccentric masses 276 in rotation. The acceleration of the eccentric masses in the cutting plane produces a periodic force of the blade holder which results in reciprocation. The eccentric masses are mounted on a countershaft which can be supported in the blade holder by ball bearings. Axial thrust of the rotating cable flexible shaft moves the blade in translation. This arrangement is both simple and lightweight and free from sliding contacts.

In use, the suction ring is positioned on the eye of the patient in surrounding relationship to the eye. The frame and blade assembly are positioned at one longitudinal end of the applanator, which is then mounted to the suction ring. When a vacuum is applied to the suction ring via suction line 340, the applanator is drawn down on the eye (which is drawn up through aperture 336) to flatten the cornea. The motor is then actuated to turn the wire within the Bowden cable and begin rotating the countershaft and counterweights. The offset weight of the countershaft and counterweights cause the frame to move side to side on the applanator, constrained by the guides in abutment with the edge of the applanator. The offset weight of the countershaft and counterweight causes the blade holding frame blade to move from side-to-side. As the frame moves from side-to-side, the blade moves therewith, causing in turn a cutting action moving about 1 mm. The applanator remains in a fixed position over the eye, held by the cleats to the suction ring, as the frame carrying the blade is advanced longitudinally therealong by pushing on the wire. The frame is advanced or pulled rearwardly in the tracks by movement of the wire relative to the sheath, the wire being moved either manually by the surgeon pushing the remotely positioned motor or through the use of a conventional actuator such as a micro controller coupled to a stepper motor for incrementally advancing the motor coupled to the internal wire.

Other Pressure Sensor Configurations

Intraocular pressure can alternately be measured with a strain gauge residing on the bottom surface of a counterbore in the applanator. The applanator is counterbored from above to form a thin diaphragm on the cornea side of the applanator.

A specially constructed strain gauge rosette is bonded to the surface of the diaphragm within the counterbored hole. The rosette constitutes a full Wheatstone bridge. Electrical output signal is approximately 300 microvolts.

Figure 25:
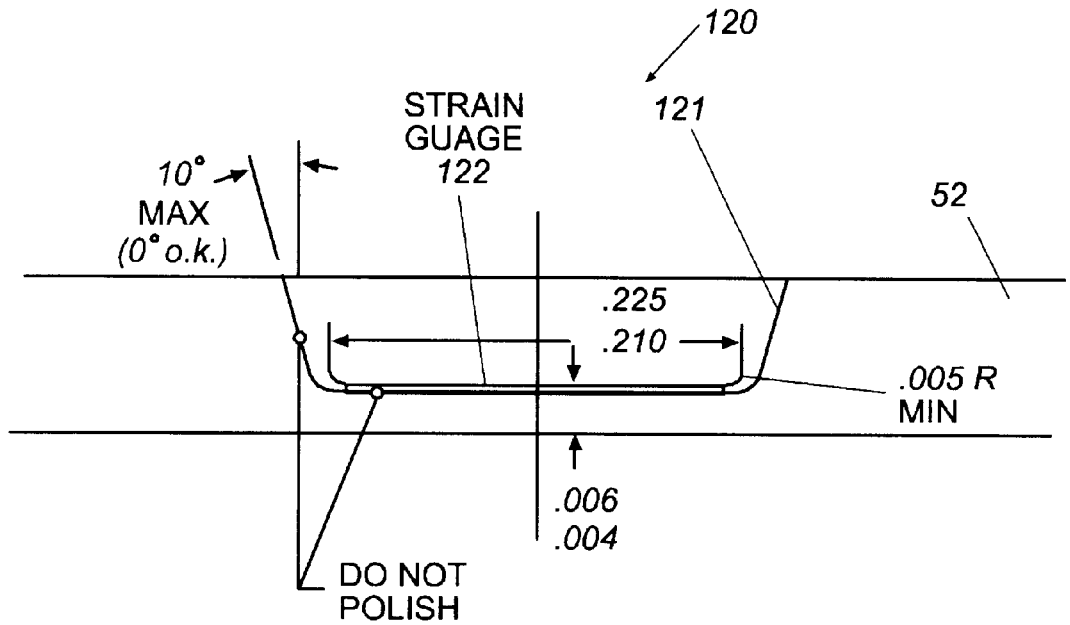
FIG. 25 is a side cross sectional view of an applanator plate 52 including a second IOP transducer configuration 120, which includes a rosette strain gauge 122 in the bottom of a counterbore hole 121 drilled into the non-operating surface of the applanator plate 52.
Figure 26:
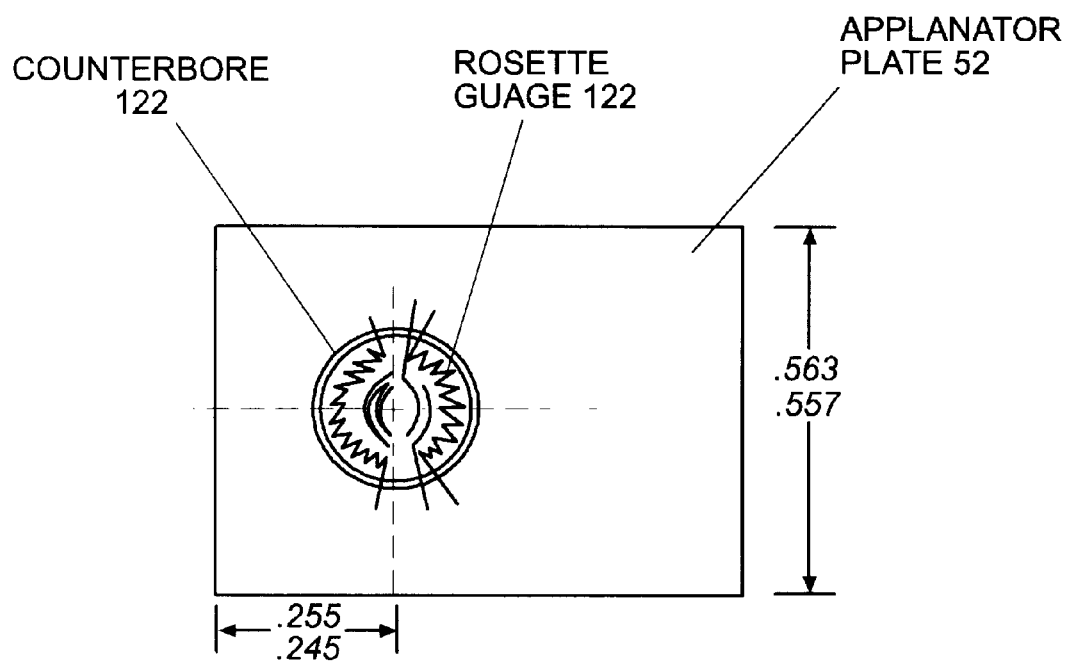
FIG. 26 is a top plan view of an applanator plate 52 including a second IOP transducer configuration 120, which includes a strain gauge 122 in the bottom of a hole 121 drilled into the non-operating surface of the applanator plate 52.

As may be seen in FIGS. 25–26, the applanator may have a transducer attached to its upper surface with leads for connection to a strain monitoring device to permit the surgeon to monitor the fluid pressure within the eye during surgery.

An exemplary transducer useful in this regarding is Mode #EA-XX-228JC-120 by Measurements Group of Raleigh, N.C.

Second Alternate Embodiment—FIGS. 33–37

FIGS. 33–37 are views of further alternate embodiments according to the present invention.

Figure 33:
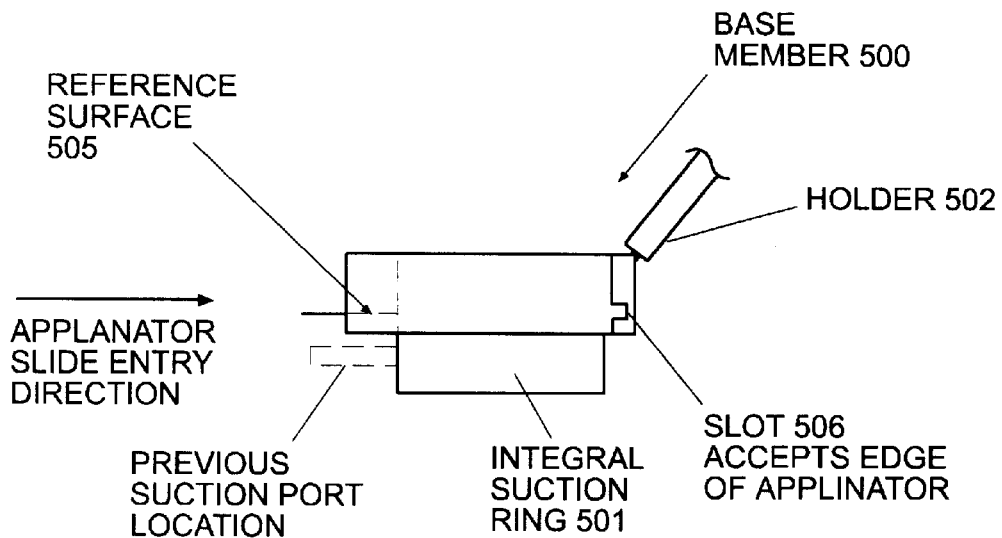
FIGS. 33–37 are views of further alternate embodiments according to the present invention.

FIG. 33 is a side elevational view of an alternate base configuration 500, which includes an inclined upper holder 502, which is rigidly attached through the body of the alternate base configuration 500 relative to an integral suction ring 501. As reference surface 505 is provided on the left, and a slot 506 is provided on the right, which as described below will accept an applanator plate assembly through a left-to-right sliding motion. This configuration does not allow for height adjustment of the applanator plate.

Figure 34:
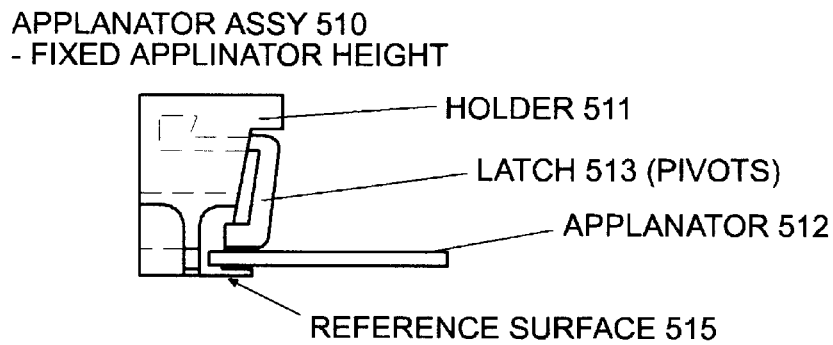

FIG. 34 is a partial side partial cross-sectional view of an applanator assembly 510 according to an alternate configuration. This assembly 510 includes a holder 511, a latch 513 pivotably attached to the holder 511, and an applanator plate 512 rigidly attached to the holder 511. The latch 513 is configured to move to allow the applanator holder and applanator plate to be moved together into place, while release of the latch engages a portion of an associated base framework, such that the applanator is held in place relative to the base framework such as 500. The configuration of FIG. 34 may be used in conjunction with the configuration of FIG. 33, and as noted above a rigid configuration which does not allow adjustability of the plate is contemplated.

Figure 35:
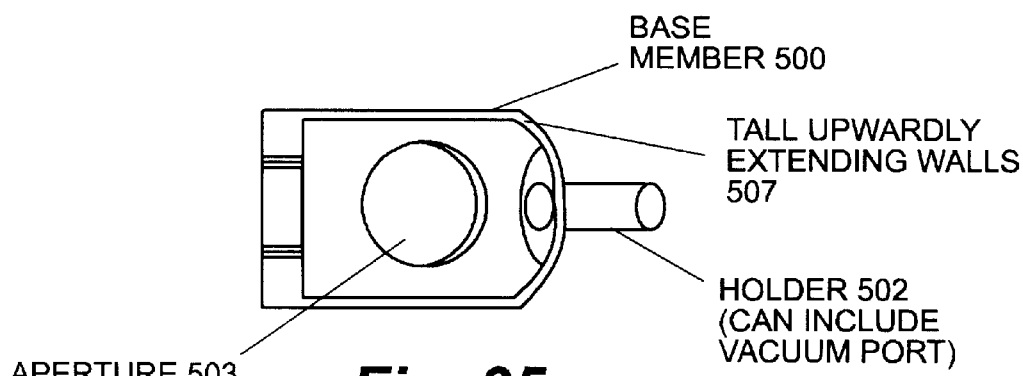

FIG. 35 is a top elevational view of the configuration shown in FIG. 33, with an aperture 503 shown, and the holder 502 shown. It may be understood that the edges or walls 507 of the base in this configuration may rise higher than earlier versions, to preclude the introduction of foreign materials which may tend to jam mechanisms working therein.

Figure 36:
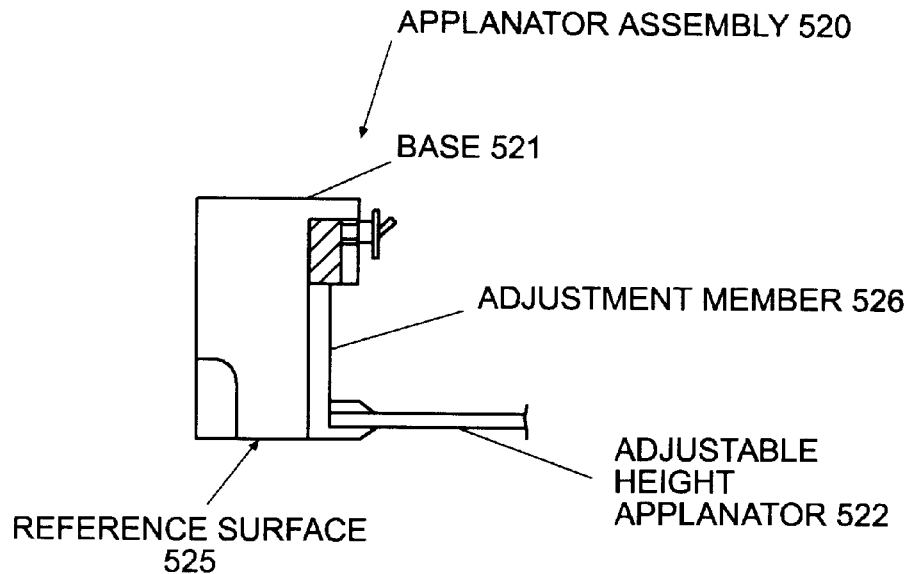

FIG. 36 is a illustrative view of an applanator assembly 520 which includes an adjustability feature. By height adjustment of an intermediate adjustment member 526 which holds the applanator 522, the applanator plate can be raised and lowered with respect to the main holder base 521.

Figure 37:
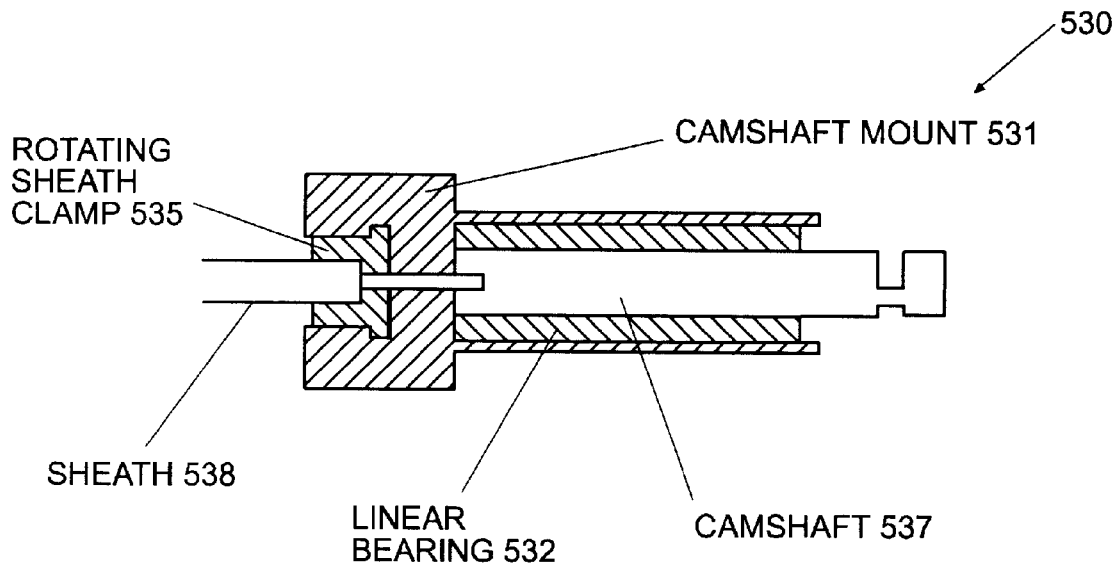

FIG. 37 is a partial side illustrative view of a modular cable drive assembly 530, which includes the use a rotating sheath clamp 535, which is allowed to rotate relative to a camshaft mount 531, to remove rotation torque which the surgeon may feel when manipulating the device. As may be understood, longitudinal movement of the rotating sheath clamp 535 is restricted due to its intimate engagement with the camshaft mount 531, but it is allowed to rotate relative to the camshaft mount 531. Also shown is a cam shaft 537, a linear bearing 532, and a sheath cable including a sheath 538.

Miscellaneous Comments

The keratome apparatuses according to the present were conceived to fill the need for a microkeratome dedicated to the dissection of a corneal flap required for ophthalmic surgical procedures. Consultation with surgeons led to the following list of preferences:

1) The instrument should be small, and without excessive volume and mass. In currently available microkeratome devices, the weight of a heavy motor extending many centimeters from the center of the fixation device applies a torque to the eye/keratome interface which tends to compromise fixation.
2) Bulky wires or tubes, which apply a torque as mentioned above, should be eliminated.
3) Obstruction to the view of the surgical field should be minimized.
4) Mechanisms which might catch or pinch the eyelids and lashes should be eliminated.
5) There should be a continuous measurement and display of interocular pressure (IOP).

In order to reduce weight and overfusing mass, under the invention the drive motor have been removed from the microkeratome and placed in a console. A single drive cable provides driving force with a flexible drive member made of a single strand or braided steel wire.

Conclusion

Therefore it may be seen that the present invention provides an improved microkeratome for use in lamellar corneal surgery.

What is claimed is:

1. A microkeratome device for use with an eye, said device comprising;
    a base assembly including a suction ring for attachment to said eye;
    an applanator assembly for contacting said eye;
    a knife assembly including a knife having a cutting edge. said eye configured for movement along its cutting edge axis and transverse to its cutting edge axis; and
    a drive assembly for driving said knife assembly such that said knife oscillates along its cutting edge axis, said drive assembly including an elongate sheathed cable, said sheathed cable operably attached to said knife and configured to allow movement of said knife both along said cutting edge axis and also transverse to said cutting edge axis by use of a single core element within said sheath, which can be both rotated within said sheath to cause said knife to oscillate and cut said eye and also moved longitudinally along and within the length of said sheath to cause said knife to move transverse to its cutting edge axis.

2. A microkeratome device, for use with an eye said device comprising;
    a base assembly including a suction ring;
    an applanator assembly for attachment relative to said eye, said applanator assembly including an applanator plate which defines an applanation surface for contacting and applanating said eye;
    a knife assembly movable relative to said applanator assembly, said knife assembly including a cutting edge for cutting the corneal epithelium of said eye thereby creating a flap;
    a shoe movable relative to said applanator assembly, said shoe being separate from but configured to move along with and in front of said knife assembly thereby separating the corneal epithelium of said eye from the applanation surface which allows the flap to pass between the shoe and the knife assembly; and a drive assembly for driving said knife assembly such that an eye can be cut.

3. A microkeratome device for use in conjunction with a remote vacuum source, said device comprising;

a base assembly including a suction ring, said suction ring including a first, vacuum-generating, port for use in conjunction with said vacuum source to provide suction sufficient to cause said suction ring to be attached to an eye, said suction ring also including a second, vacuum-monitoring, port independent of said vacuum source and configured to be routed to a vacuum gauge to detect vacuum but not to generate vacuum;

an applanator assembly;

a knife assembly; and a drive assembly for driving said knife assembly such that said eye can be cut.

4. A microkeratome device for use in applanating and cutting an applanated eye, said device comprising;

a base assembly including a suction ring defining an opening therein which permits a portion of said eye to pass therethrough;

an applanator assembly having an applanator plate, said applanator assembly being hingedly removable and detachable relative to said base assembly such that while said base assembly is attached to said eve said applanator assembly may be pivoted from a first, applanating, position, wherein said applanator plate covers the opening completely to a second, removable, non-applanating position, and then removed from said base assembly while said base assembly is still in place on said eye, but said applanator assembly cannot be removed when said applanator assembly is in said first, applanating, position;

a knife assembly; and a drive assembly for driving said knife assembly such that an eye can be cut while said applanator assembly is in said first, applanating, position.

* * * * *

UNITED STATES PATENT AND TRADEMARK OFFICE
CERTIFICATE OF CORRECTION

PATENT NO. : 6,126,668
DATED : October 3, 2000
INVENTOR(S) : Bair et al.

Page 1 of 1

It is certified that error appears in the above-identified patent and that said Letters Patent is hereby corrected as shown below:

Title page,
[56] References Cited, FOREIGN PATENT DOCUMENTS, "European Patent Office" should read --WIPO--.

Column 2,
Line 20, "Hoffman et al." should read --Hoffmann et al.--;
Lines 21-22, should read --"WO 93/06783--

Column 16,
Line 35, after "comprising" the semi-colon (;) should be a colon (:);
Line 40, after "edge" the period (.) should be a comma (,);
Line 55, after "device" cancel the comma (,) and after "eye" insert a comma (,);
Line 56, after "comprising" the semi-colon (;) should be a colon (:).

Column 17,
Line 8 and line 23, after "comprising" the semi-colon (;) each occurrence, should be a colon (:).

Column 18,
Line 7, "eve" should read --eye--.

Signed and Sealed this

Fourteenth Day of August, 2001

*Attest:*

*Attesting Officer*

NICHOLAS P. GODICI
*Acting Director of the United States Patent and Trademark Office*